United States Patent
Boken

(10) Patent No.: US 7,318,350 B2
(45) Date of Patent: Jan. 15, 2008

(54) VALVE MONITORING SYSTEM AND METHOD

(76) Inventor: Michael Boken, 16 The Hythe Staines, Middlesex, TW18 3JA (GB)

(*) Notice: Subject to any disclaimer, the term of this patent is extended or adjusted under 35 U.S.C. 154(b) by 208 days.

(21) Appl. No.: 11/134,182

(22) Filed: May 20, 2005

(65) Prior Publication Data
US 2005/0257618 A1 Nov. 24, 2005

(30) Foreign Application Priority Data
Feb. 21, 2004 (GB) .................................. 0411447

(51) Int. Cl.
G01N 29/14 (2006.01)
F16K 37/00 (2006.01)

(52) U.S. Cl. .............................. 73/587; 73/592; 73/593

(58) Field of Classification Search .................. 73/587, 73/592, 593
See application file for complete search history.

(56) References Cited

U.S. PATENT DOCUMENTS

| | | | | |
|---|---|---|---|---|
| 4,429,578 A | * | 2/1984 | Darrel et al. .................. | 73/659 |
| 4,523,286 A | * | 6/1985 | Koga et al. .................. | 702/183 |
| 4,559,828 A | * | 12/1985 | Liszka .......................... | 73/658 |
| 5,008,841 A | * | 4/1991 | McElroy ....................... | 702/39 |
| 5,041,989 A | * | 8/1991 | Kataoka et al. ............... | 702/39 |
| 5,154,080 A | * | 10/1992 | Hill et al. ...................... | 73/597 |
| 5,616,829 A | * | 4/1997 | Balaschak et al. ............. | 73/46 |
| 5,650,943 A | * | 7/1997 | Powell et al. .................. | 702/51 |
| 6,189,384 B1 | * | 2/2001 | Piety et al. .................... | 73/592 |
| 6,260,004 B1 | * | 7/2001 | Hays et al. .................. | 702/183 |
| 6,499,349 B1 | * | 12/2002 | Aronsson ...................... | 73/659 |
| 6,666,093 B2 | * | 12/2003 | Morganti ...................... | 73/587 |
| 7,069,183 B2 | * | 6/2006 | Schluecker et al. .......... | 702/185 |
| 2005/0126639 A1 | * | 6/2005 | Ens et al. .................... | 137/554 |

* cited by examiner

*Primary Examiner*—Hezron Williams
*Assistant Examiner*—Rose M Miller
(74) *Attorney, Agent, or Firm*—Craig A. Fieschko, Esq.; DeWitt Ross & Stevens S.C.

(57) ABSTRACT

A valve monitoring system includes an alert generation system and a memory. The memory encodes baseline acoustic emission data on the valve for a predetermined period of operation. The alert generation system is arranged to receive acoustic emission data for the valve, compare the received acoustic emission data for the valve with the baseline acoustic emission data encoded in the memory and identify valve anomalies in dependence on differences in the received acoustic emission data and the baseline acoustic emission data.

20 Claims, 16 Drawing Sheets

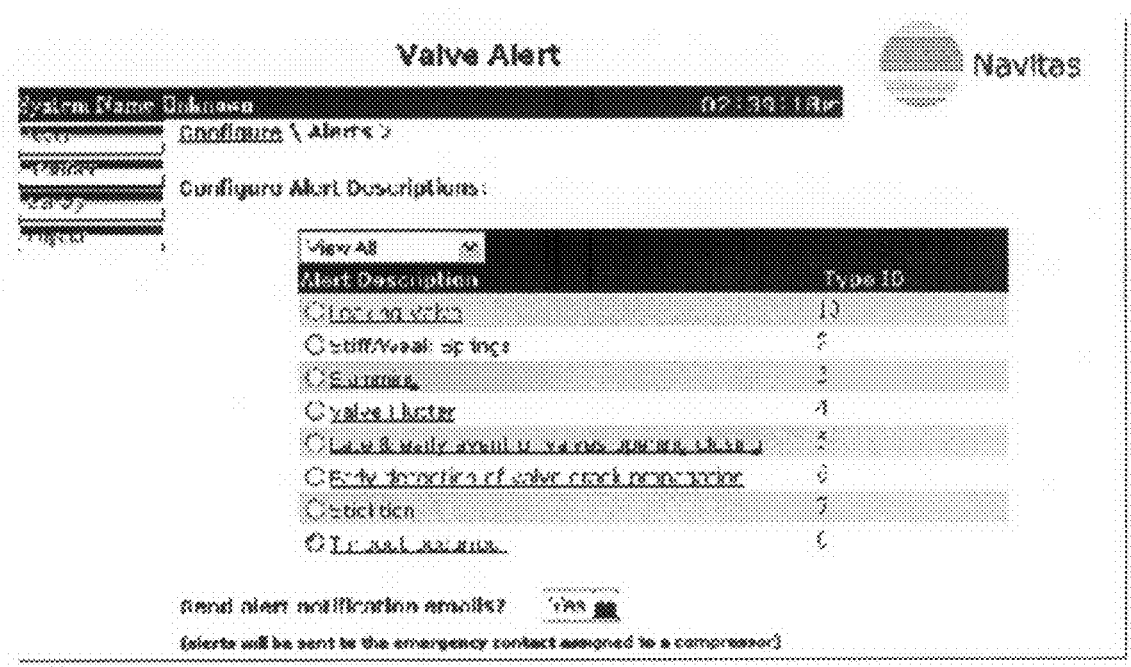
Fig. 25
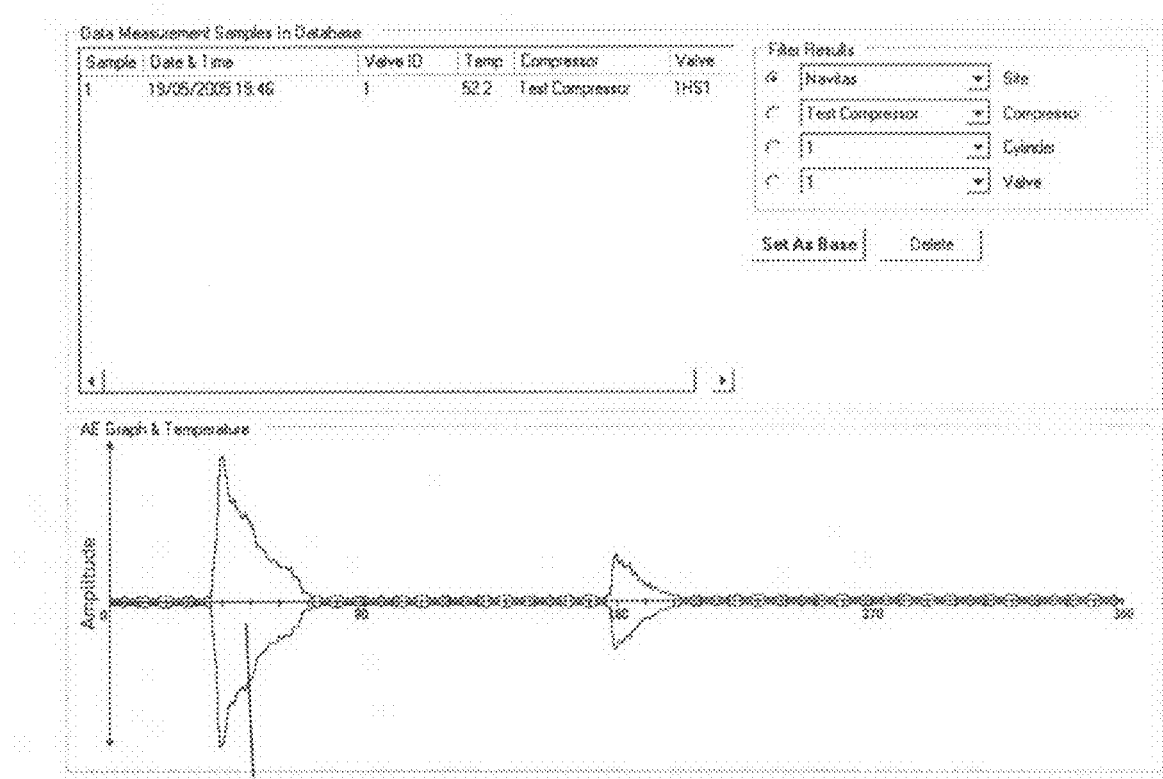
300  Fig. 26

VALVE MONITORING SYSTEM AND METHOD

FIELD OF THE INVENTION

The present invention relates to a method and system suitable for monitoring and analysis of valve conditions.

BACKGROUND TO THE INVENTION

Valves are used in all manner of machinery to prevent or permit passage of solid, liquid or gaseous matter from one area to another. Because of the mechanical nature of most valves and also due to the harsh environment in which a valve is typically operated, valve components can have limited and unpredictable lifetimes. Furthermore, microscopic faults in valve components that are undetectable at the time of manufacture can grow during use of the component resulting in a loss in valve performance or complete valve failure.

Many monitoring systems available to the compressor industry, while sophisticated, are either costly to install and maintain or require specialist manpower to collect data, process and analyse.

Compressor valves are the most critical parts of a piston compressor and are key to its overall availability, with valve problems reportedly the primary reason for reciprocating compressor shutdowns. Compressor valves fail for a variety of reasons, which can generally be divided into design and operating factors. Valve design could contribute if the wrong type for a particular application is fitted, or if operation failures occur related to the process gas conditions and how the compressor is run and maintained.

Experience has shown that regular monitoring of a compressor can identify and warn operators of significant situations that would otherwise not be detected. Nearly 75% of unscheduled shutdowns on existing reciprocating compressors can be associated with cylinder end components. Identifying those components can pay dividends in increased reliability and reduced maintenance costs. Frequently however, compressor deterioration remains hidden until a costly secondary failure occurs.

For example, in the case of reciprocating compressor valves, various different problems can be experienced, the major ones being:
1. High valve lift
2. Excessive impact velocity
3. Changed spring rate
4. Particulate ingestion
5. Oil stiction.
6. Leakage In a chemical or other large scale plant, hundreds or thousands of valves may be used. The valves may be interconnected in such a way that it is not always possible to identify which valve may have failed or is experiencing problems. As valves are often mounted in inaccessible or remote areas of a plant, even if a failure is identified, it may take time to locate and change the failed components, possibly resulting in significant losses to the plant.

Typical industrial sites do not employ maintenance engineers full-time, as this can be costly. The downside of this is that when a compressor failure occurs, an unscheduled shutdown is required until a maintenance engineer resolves the issue. This can lead to long down-times, as appointments need to be scheduled and parts may need to be ordered, in many cases this disturbs the flow of the production line. The unscheduled shut-downs could be eliminated if it were possible to detect the fault before it affects the overall performance of a compressor.

To detect an incipient fault in a system before it materializes into a system failure, one technique known as condition monitoring is employed. Condition monitoring involves the observation, measurement and/or trending of data in order to indicate the current and future condition of a system Monitoring is inefficient as it is time and resource-consuming, as well as being prone to human error (it is very possible to mix up valves due to the large number of required measurements). Collection of data for input into a monitoring system in large sites with many compressors can be very time consuming, and may require multiple operators to cope with the amounts of measurements required. Indeed, even on sites where there are dedicated maintenance personnel, monitoring is likely to be very low on the list of priorities and in most cases will happen sporadically, possibly once a problem has been identified as opposed to in real time.

In the case of compressors, in the event of a valve failure, the entire compressor must be shut down for unscheduled maintenance, in order to replace the damaged valve(s). Since these shut-downs are generally unscheduled, they end up creating a long period of downtime for the compressor, since a maintenance engineer must be called out to evaluate the situation and repair/replace the damaged parts. Valve failures account for the majority of compressor down-times. Being able to detect incipient failure of a valve before the effects of the failure become apparent allows for scheduled maintenance to take place, and is extremely desirable.

SUMMARY OF THE INVENTION

According to an aspect of the present invention, there is provided a valve monitoring system including an alert generation system and a memory, the memory encoding baseline acoustic emission data on the valve for a predetermined period of operation, the alert generation system being arranged to receive acoustic emission data for the valve, compare the received acoustic emission data for the valve with the baseline acoustic emission data encoded in the memory and identify valve anomalies in dependence on differences in the received acoustic emission data and the baseline acoustic emission data.

The valve may be mounted in a reciprocating compressor, in which case the predetermined period of operation comprises a 360° rotation of the crank of the reciprocating compressor.

The system may further comprise a sensor mounted to obtain acoustic emission data on the valve and a data collector arranged to communicate with the sensor to obtain said acoustic emission data.

The data collector may comprise a portable device including an input device for receiving an identifier for the valve to which a sensor is mounted, a memory for storing said identifier and said acoustic emission data and at least one communication system for communicating with the sensor and the alert generation system. The identifier may include a barcode displayed in a location near to the valve, in which case the data collector includes a barcode reader. The identifier may include an RFID tag integrated into said sensor, in which case the data collector includes an RFID tag reader.

The alert generation system and memory are preferably remote from the sensor. The data collector may be integrated with the sensor, the data collector including a communications system to communicate said acoustic emission data to the alert generation system.

The portable device may include a processor arranged to remove negative waveform components and high frequency carrier components of the acoustic emission data prior to storage in the memory.

The system may include a plurality of data collectors and a plurality of intermediate nodes, each of said plurality of data collectors being arranged to communicate its acoustic emission data to a predetermined one of said plurality of intermediate nodes, each intermediate node being arranged to communicate received acoustic emission data to said alert generation system.

The data collector may include a processor arranged to remove negative waveform components and high frequency carrier components of the acoustic emission data prior to communication of the acoustic emission data.

The system may further comprise an alert notification system arranged to provide notification to a contact associated with said valve in response to identification of a valve anomaly, notification comprising at least one of:
  an email message, an instant message, an SMS message or a pre-recorded telephone message.

The system may further comprise a user interface arranged to visually display an indication of anomalies identified for the valve.

The indication may comprise a hierarchy of warning lights such as traffic lights, the warning light illuminated being dependent on the severity of the anomaly identified.

The user interface may include a schematic representation of monitored valves, the schematic representation being visually associated with the indication for the respective valve.

According to another aspect of the present invention, in a valve monitoring system, a method for monitoring valves comprises:
  obtaining a baseline acoustic emission signal for a valve for a predetermined period of operation;
  obtaining a further acoustic emission signal for the valve for the predetermined period of operation;
  comparing the baseline acoustic emission signal with the further acoustic emission signal;
  identifying valve anomalies in dependence on differences between the baseline acoustic emission signal and the further acoustic emission signal.

The method may further comprise:

mounting an acoustic emission sensor on a valve of a reciprocating compressor, wherein the predetermined period of operation comprises a 360° rotation of the crank of the reciprocating compressor.

The method may further comprise:
  collecting the further acoustic emission signal from the sensor using a portable data collector arranged to communicate with the sensor; and,
  downloading the acoustic emission signal from the portable data collector to a system remote to the sensor for said comparison and identification steps.

The method may further comprise:
  removing negative waveform components and high frequency carrier components of the further acoustic emission signal prior to downloading.

The method may further comprise:
  collecting the further acoustic emission signal from the sensor at a data collector integrated with the sensor and mounted on the valve; and,
  transmitting the acoustic emission signal to a system remote to the sensor for said comparison and identification steps.

The method may further comprise:
  removing negative waveform components and high frequency carrier components of the further acoustic emission signal prior to transmitting.

The present invention seeks to provide a valve monitoring system and method able to provide monitoring data online or via a portable handheld unit so that faults and other discrepancies can be identified before they escalate into larger valve or plant failures. Preferably, the present invention includes a user interface including a simplified alert to advise a user of problems with a valve or system. The alert may be in the form of a traffic light. In this manner, the present invention seeks to provide a system for condition monitoring and fault diagnosis for improving system availability and reliability.

Acoustic emission refers to the measurement of surface acoustic waves generated by the release of energy from within a material. AE monitoring has significant potential applications in the assessment of damage to structures, structural integrity, the operation of processes and the identification of changes within materials.

The present invention seeks to apply AE methods to achieve a cost effective product that:
1. Reduces system cost of ownership.
2. Utilizes both off-line and online monitoring for data acquisition.
3. Calculates rate of leakage/gas passing in valves.

Prior techniques have required more sophisticated analysers to collect data and skilled engineers to analyse it. However, the present invention seeks to provide a more cost effective and simplified process that can detect valve anomalies quicker, more easily and more cheaply.

Although embodiments of the present invention are discussed below with reference to valves of reciprocating compressors, valves in any application, system or environment could be monitored.

Benefits to Industry include:
a) Identifying compressor valve anomalies prior to failure
b) Eliminating the need for high costs consultants
c) Reduction in cost of ownership of analysers
d) Ensuring safer operation of plant
e) Environmental issues
f) Ease of operation and use
g) Increase in Machinery Life
h) Reduction in maintenance costs

BRIEF DESCRIPTION OF THE DRAWINGS

Embodiments of the present invention will now be described in detail with reference to the accompanying drawings, in which:

FIGS. 14 to 25 are screen shots from an alternative online user interface provided by the alert generation system; and, FIGS. 26 to 29 show an alternate layout of a user interface provided by the alert generation system.

DETAILED DESCRIPTION

Although many systems and applications are dependent on valves, valves used in engines, compressors and the like are among the most hard worn.

One type of compressor is known as a reciprocating compressor. A reciprocating compressor has a cylinder shaft that moves in a back and forth motion. These are used in industrial sites, to pump gases or liquids. A compressor has a number of cylinders, each with a number of valves. In the middle, a flywheel, powered by some sort of motor (electric or gas), moves a piston back and forth, repeating its cycle with every rotation. The start of this cycle is known as Top Dead Centre (TDC), occurring at crank angle 0°. At this point, the piston is at the head end of the cylinder.

As the piston moves towards the crank end, the head-end suction valves open, allowing gas or liquid to flow into the cylinder and the pressure on the crank-end side of the piston forces discharge valves to open, releasing the gas on that side of the piston. At 180°, the piston is at Bottom Dead Centre (BDC). The head-end suction valves close, keeping the gas inside the cylinder. As the piston moves back towards TDC, the crank-end suction valves open, allowing gas to flow on the crank side of the piston, whilst the pressure on the head-end valves forces them open, discharging the gas.

Figure 1:
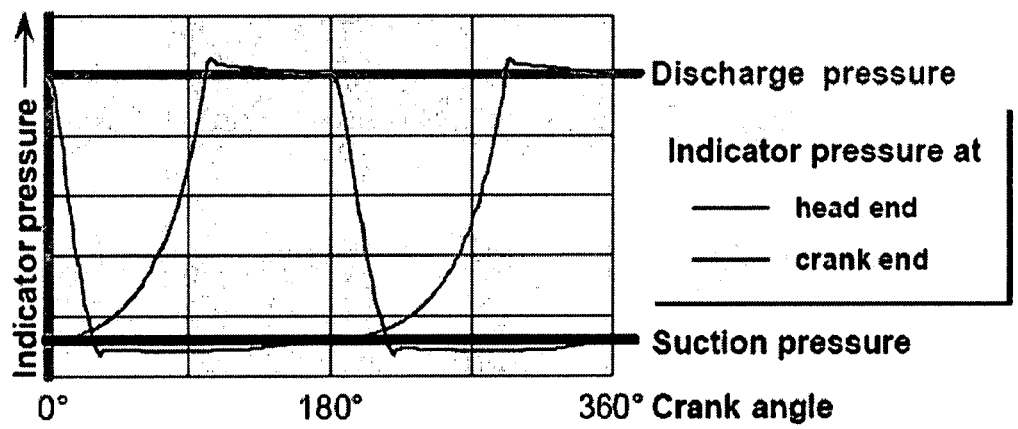
FIG. 1 is a graph plotting pressure against flywheel angle for an example reciprocating compressor.

Different events occur at different flywheel angles. The repetitive operation produces a graph with recognisable characteristics when plotting pressure as a function of the flywheel angle, an example of which is shown in FIG. 1. The recognisable characteristics form a baseline signature for a valve, which is also referred to herein as a fingerprint for the valve. The fingerprint remains substantially unchanged until a change in the valve's closed system occurs, such as a crack or the springs weakening.

Monitoring the vibrations of a valve surface using an acoustic emission (AE) sensor, a graph with the same shape as that of FIG. 1 is found, plotting the vibrations as a function of the crank angle. These graphs can be analysed and compared to a predetermined baseline signature of the valve when it is working, to check for large deviations from the baseline signature. This allows for early detection of the following valve anomalies:

Leaking Valve
Valve Slamming
Stiff/Weak Springs
Valve sticktion

These different anomalies produce distinct deviations on the valve's fingerprint, even when the actual effects of the fault are not affecting the overall performance of the system.

The failure modes discussed above can be associated with detectable AE of either the burst or continuous type. In the case of discrete AE bursts, the important factors to study are the energy contained within a burst and its time of occurrence within a compression cycle. For the continuous AE signal, the power content is an important parameter for investigation. Often the two types of AE appear together, thus rendering the signal processing and analysis more sophisticated.

High valve lift has the problem that it lowers the pressure drop across the valve producing a continuous AE signal of lower power content. The higher the lift, the greater is the impact velocity of the valve with its seat and the stronger is the AE burst that occurs with a slight time delay.

Changed spring rates influence the valve impact velocity the time of impact of the valve with its seat. Both factors cause a change in the strength of energy in the AE burst and in its time of occurrence. Particulates that get in the way of the valve and seat will prevent a proper sealing of the compression chamber; the ensuing leakage will produce a continuous AE signal with a power level affected by the degree of leakage.

Since oil stiction inhibits valve opening, causing the valve to slam open when the force created by the differential pressure exceeds the stiction force, the sudden action creates an AE burst with strong energy and the timing of its opening is also delayed.

As there are a number of valves in a reciprocating compressor, it is possible to make use of the time signals to identify the causes of different AE bursts with the source location method developed in the System project. Due to the fact that AE signals are inherently variable, the approach to the study of the timing and of the AE signal contents themselves are based on statistical analysis of the underlying distribution of such features.

Figure 2:
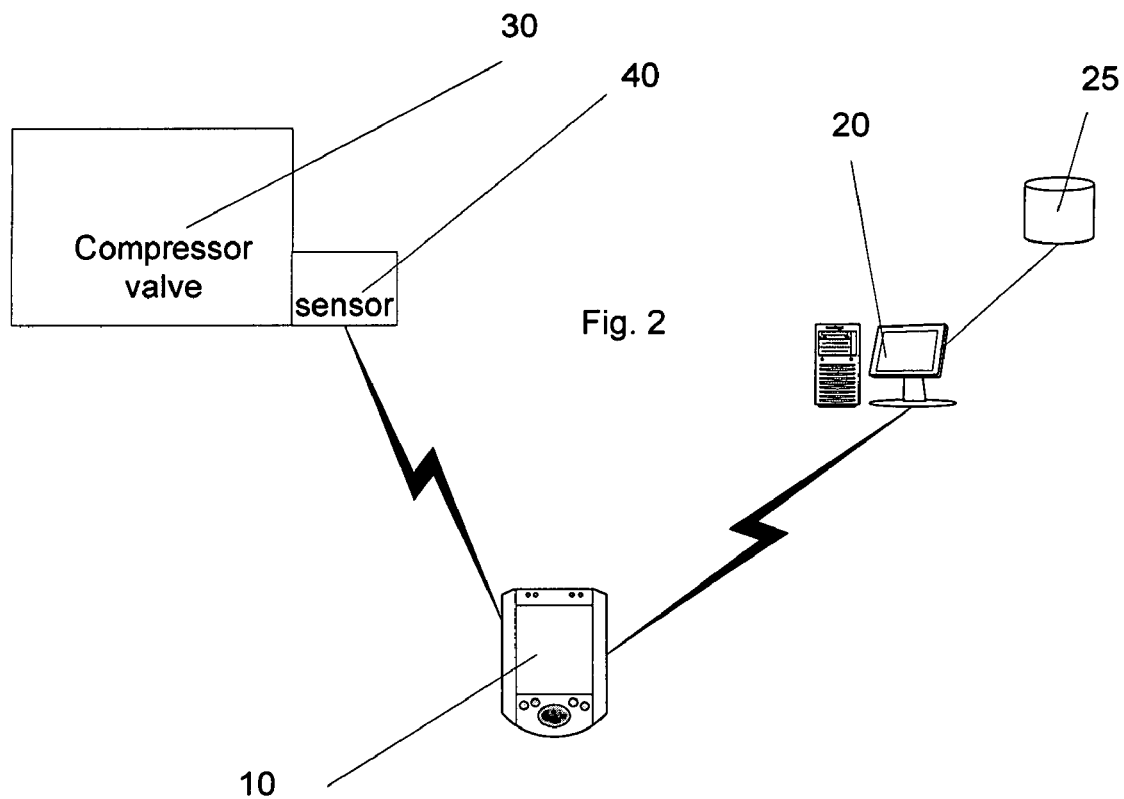
FIG. 2 is a schematic diagram of a valve monitoring system according to an embodiment of the present invention.

FIG. 2 is a schematic diagram of a valve monitoring system according to an embodiment of the present invention.

The valve monitoring system includes a data collector 10 and a remote alert generation system 20.

This embodiment is particularly useful for collecting valve data from compressor valves 30 and identifying problems associated with a valve before it fails. Acoustic emission data sensors operating at approximately 150 KhZ are used for obtaining data from the valves, although many other sensor types could be used.

The sensor 40 could be built into the valve machinery or alternatively mounted at appropriate points close to the valve in question to allow capturing of AE signals. The sensors may include a memory so that AE signals can be captured and stored for a predetermined time.

The sensor 40 can include a local interface for coupling to a handheld data collector or alternatively they could include a wired or wireless data network connection such as Bluetooth, IEEE 802.11 or the like.

In the embodiment of FIG. 2, the data collector 10 is a small hand held unit which is capable of capturing samples from many sensors over a period of time (for example as a technician moves round a site visiting each sensor). The hand held unit may be arranged to process the samples to identify anomalies, although preferably it merely stores them for later uploading and analysis by the alert generation system 20. The data collector 10 is preferably battery powered and has the option of recharging itself from the power supplied by the USB port when connected to a PC, server or the like.

Figure 3:
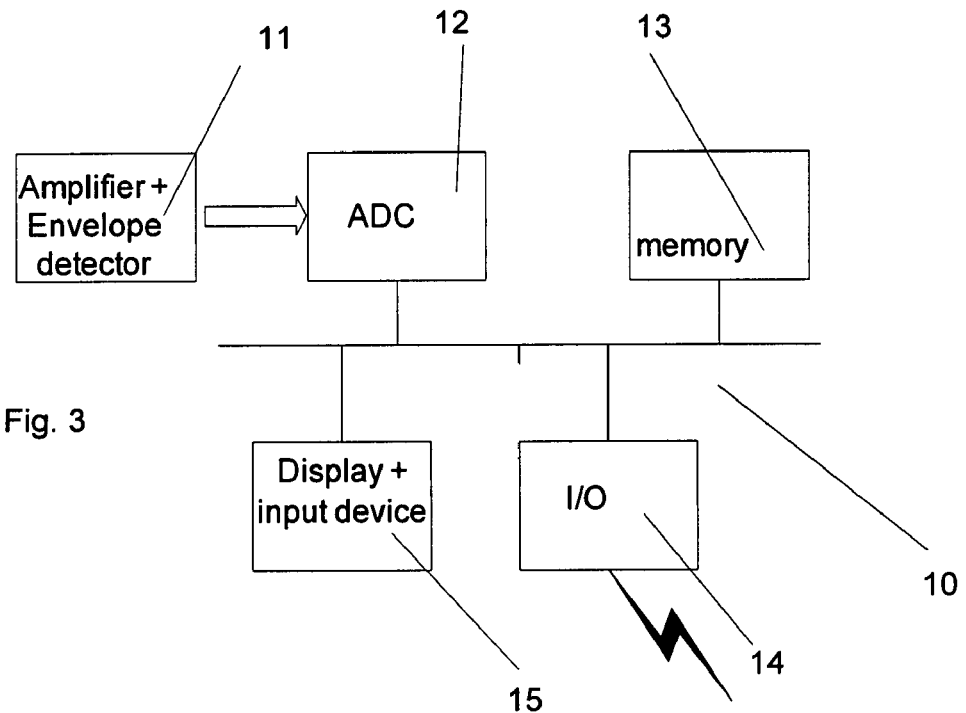
FIG. 3 is a schematic diagram of an example portable data collector suitable for use in an embodiment of the present invention.

FIG. 3 is a schematic diagram of an example portable data collector 10 suitable for use in an embodiment of the present invention.

The portable data collector 10 includes an amplifier and envelope detector 11, an analog to digital converter (ADC) 12, a memory 13 and an input/output system 14.

The amplifier is preferably either a transimpedance amplifier or FET input stage. This is followed by another high gain amplifier.

The envelope detector could be two peak detectors so that while one is peak detecting, the other is discharging. The discharge will be slightly delayed to allow the ADC 12 to sample the voltage before it is discharged. This should provide better performance than a single leaky peak detector.

The ADC 12 will require a signal conditioner stage which will convert the voltage range of the output from the envelope detector to within the limits of the upper and lower thresholds of the ADC 12. The ADC 12 will also require outputs that are able to enter a high impedance mode to allow the memory to drive the data bus when sending the samples to the PC.

Volatile memory 13 is preferably used to store the samples. This will be expandable to allow units with differing amounts of memory to be produced.

A high/full speed USB Device 14 is preferably used to operate as both the processor for I/O purposes. While the USB is not connected, it acts as a stand-alone microcontroller. The processor generates clock signals for the Envelope Detector, ADC and Memory and provides memory addresses to store the samples. The portable data collector preferably includes a display and an input device 15.

When the data collector is connected to the alert generation system 20, it will clock the samples out of the memory 13 and send them over the USB connection.

Each compressor in a plant is uniquely numbered or labelled and the technician enters the compressor number into the data collector via the input device 15 as signals are downloaded. The data collector can then be capture sample data from the sensor. The input device 15 could include a keyboard or touch screen. Alternatively, barcodes or RFID tags could be installed on each valve, in which case the input device 15 will include an appropriate scanner provided in the data collector to enable the data collector to identify what valve it is collecting data from.

The sensor 40 is plugged into the handheld data collector via a flexible lead connected to a quick release adaptor situated on the valve cover. Data including acoustic emission (AE) waveforms and temperature is gathered from each valve and stored by the data collector.

This data is then downloaded to the alert generation system 20 for analysis of the data and generation of results on the condition of each valve.

Figure 4:
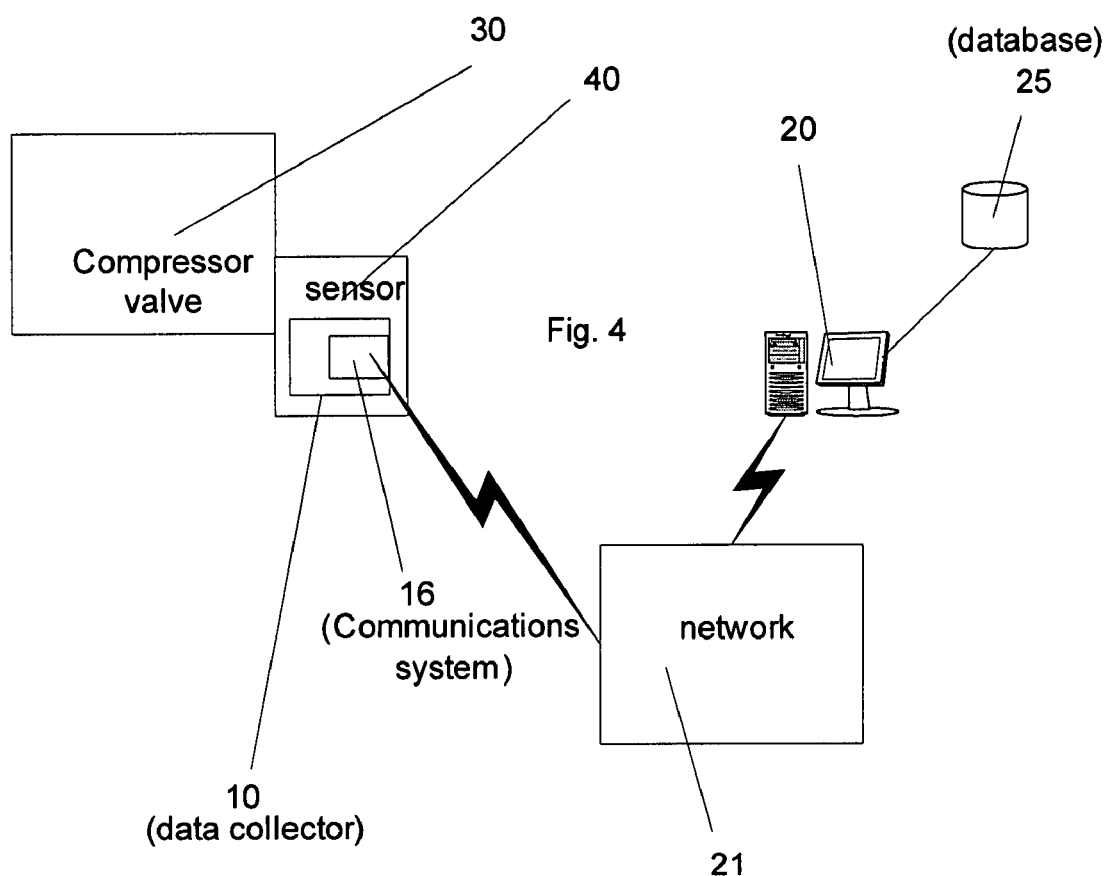
FIG. 4 is a schematic diagram of a valve monitoring system according to an alternate embodiment of the present invention.

An alternative embodiment of the present invention is shown in FIG. 4 in which the data collector 10 is integrated with the sensor at the site of the valve.

The data collector 10 includes a communications system 16 arranged to communicate the acoustic emission data to the alert generation system. Communication may be direct or via an assigned intermediate node.

During operation of the sensors in either embodiment, an immense amount of data is obtained and must be stored and/or transmitted for subsequent analysis. Purely to store the raw data of 16 bit samples 100,000 data points per valve 4 valves in one cylinder, one would need $$\frac{100{,}000 \text{ samples} * 4 \text{ valves} * (16 \text{ bits}/8 \text{ bits per byte})}{1024^2 \text{ bytes per MB}} = 0.76 \text{ MB}$$

In order to reduce this storage overhead, an envelope detection process is preferably performed on the data at the time of storing or transmission by the data collector. This process considers only the positive half of the waveform and removes the high frequency carrier. This reduces 100,000 data samples down to about 200 or 300 samples. This process could be implemented in software or hardware using operational amplifiers. If the data is reduced to 300 samples, the storage capacity needed would be:

$$\frac{300 \text{ samples} * 4 \text{ valves} * (16 \text{ bits}/8 \text{ bits per byte})}{1024^2 \text{ bytes per MB}} = 0.00229 \text{ MB}$$

Therefore, even with only 4 megabytes of RAM, you could monitor 1747 cylinders. This would also make the data collector much cheaper to produce as you wouldn't need an ADC nearly as fast. Alternatively, the reduced data size means that online monitoring and/or use of wireless data networks to transmit the data in substantially real time is possible. The reason why we need so few samples to store a demodulated signal is because the high frequency carrier has been removed, leaving a much lower frequency signal so fewer samples are needed to keep its integrity.

In the case of either embodiment discussed above, the alert generation system is preferably formed from software operating on a PC or server. The system preferably includes a database of all the valves in the plant. The database may include valve types and ID's so the software can determine which valve relates to which sample collected by a portable data collector (or received if the data collector is integrated with the sensor) and can look for different types of anomalies.

At the alert generation system 20, each sample is downloaded, compared against a predetermined baseline fingerprint for the valve held by the in the system in a valve database 25 and any relevant alerts or alarms generated and issued.

A user interface is preferably provided by the alert generation system providing a hierarchical light indicator in the form of a 'traffic light' graphic display—green indicates a good valve—yellow, a possible problem, advising closer monitoring of the valve is recommended—red indicates a problem requiring immediate attention.

Following these 'traffic lights' the technician will have an overview of all the compressors configured in the system and can immediately ascertain whether there are any valve problems on these compressors.

Having identified the compressor with a problematic valve(s), the technician can then view a graphic display of the compressor in question. The 'traffic light' graphic will display in which cylinder the problem valve is located.

Once the cylinder with a problematic valve has been located, the next screen will identify the cylinder end and exact position of the valve (or valves). The software enables further in-depth analysis, if required, as to the particular problem, ie. leaking valve, weak springs, late opening and closing etc.

Having analysed the mechanical condition of the valve and the severity of the problem, the technician can then decide on which course of action should be implemented and plan accordingly, this can prevent unexpected and often very expensive breakdowns.

Figure 5:
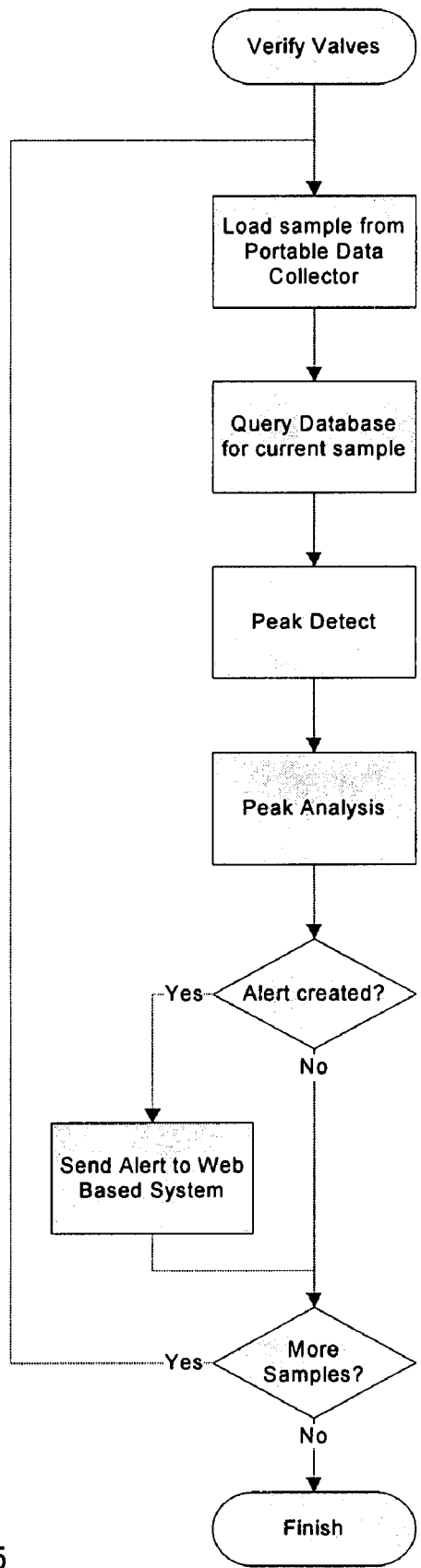
FIG. 5 is a flow diagram of operation of the alert generation system according to an embodiment of the present invention.

FIG. 5 is a flow diagram of an example method of operation of the alert generation system according to an embodiment of the present invention.

The alert generation system 20 preferably provides a web based user interface and is designed to inform the relevant people of any alerts generated and their severity. It does this via a graphical display of the compressor and a traffic light system for a quick indication of any alert. An option is also available to send an email, SMS, instant message or pre-recorded telephone message upon alert generation.

FIGS. 6 to 9 are screenshots of the user interface of the alert generation system according to an embodiment of the present invention.

Figure 6:
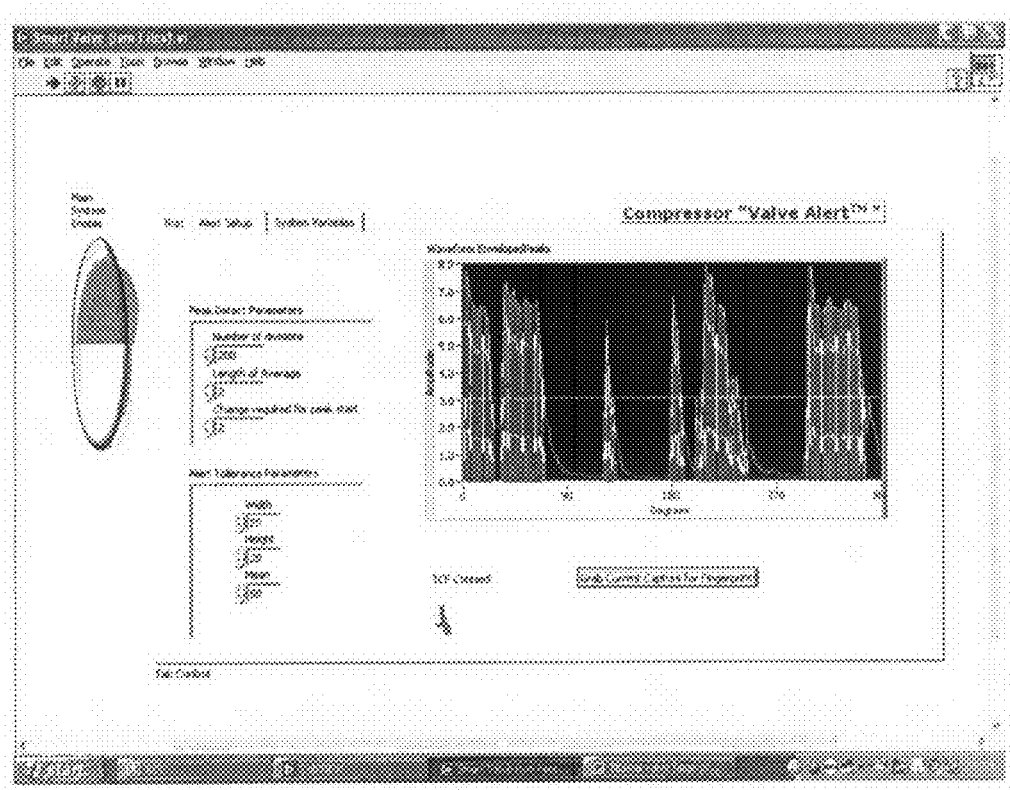
FIGS. 6 to 9 are screenshots of the user interface of the alert generation system according to an embodiment of the present invention.

FIG. 6 is an example screen shot of a user interface showing the definition of a normal valve fingerprint.

Figure 7:
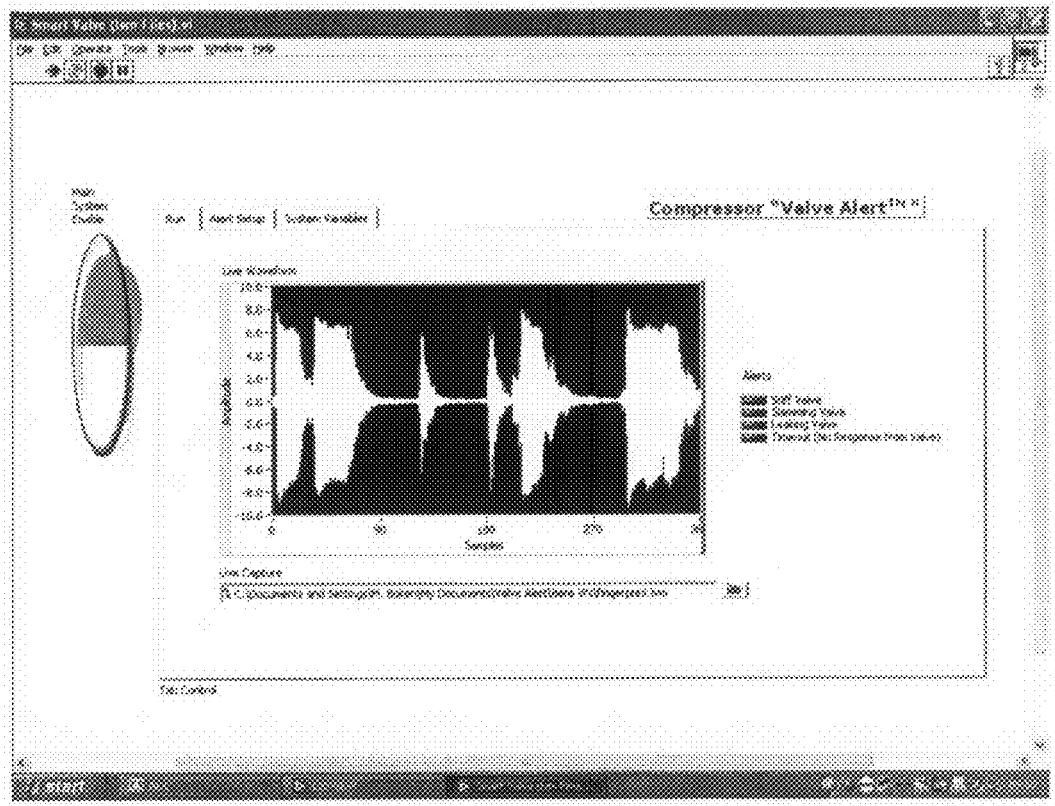

FIG. 7 is an example screenshot of a user interface showing the detection of the normal valve fingerprint and no associated alerts.

Figure 8:
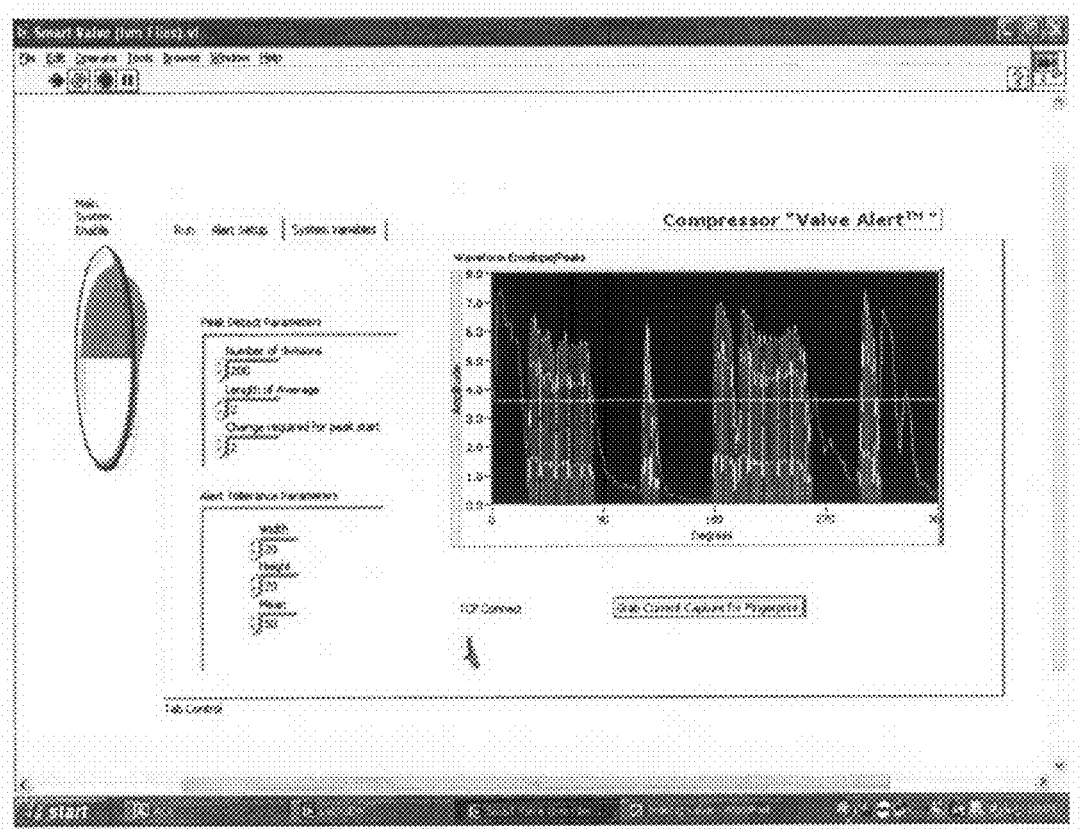

FIG. 8 is an example screenshot of a user interface showing the definition of a leaking valve fingerprint.

Figure 9:
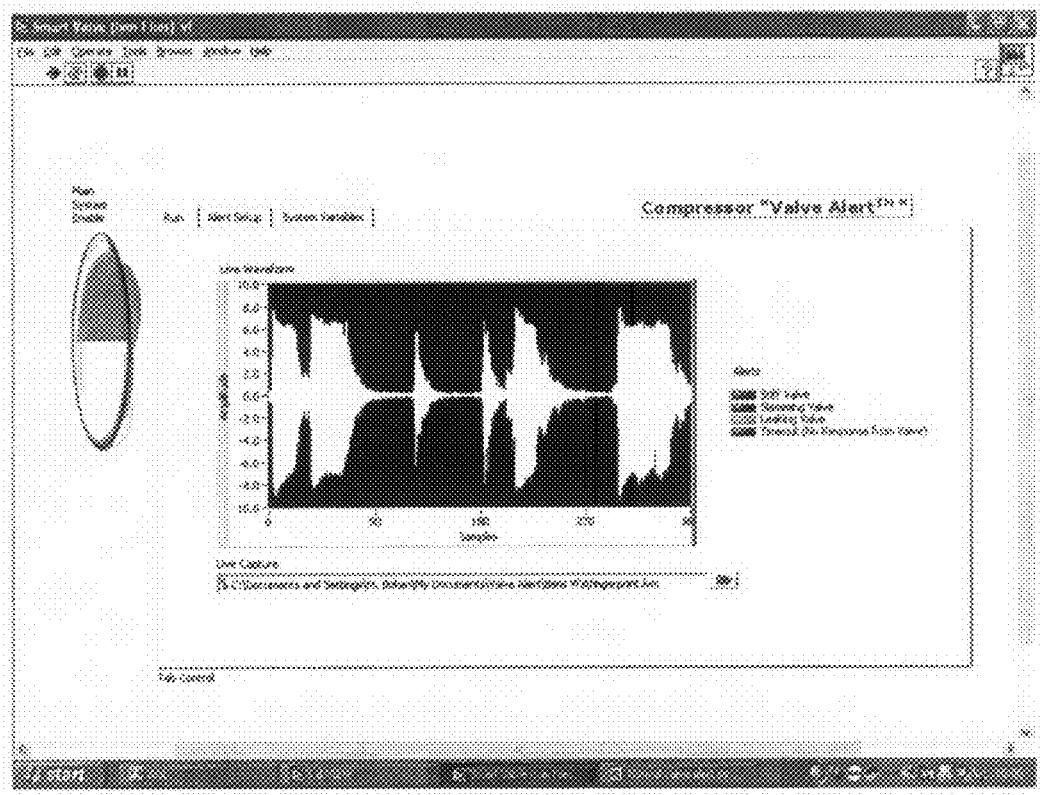

FIG. 9 is and example screenshot of a user interface showing the detection of the leaking valve fingerprint and displaying an associated alert.

FIGS. 10 to 13 are screenshots of an alternate user interface of the alert generation system according to another embodiment of the present invention. In this case, the interface has been simplified to be displayed on a PDA, mobile phone or other remote unit. It may be that only the alert traffic lights along with an identification of the valve is displayed and the waveform is omitted.

Figure 10:
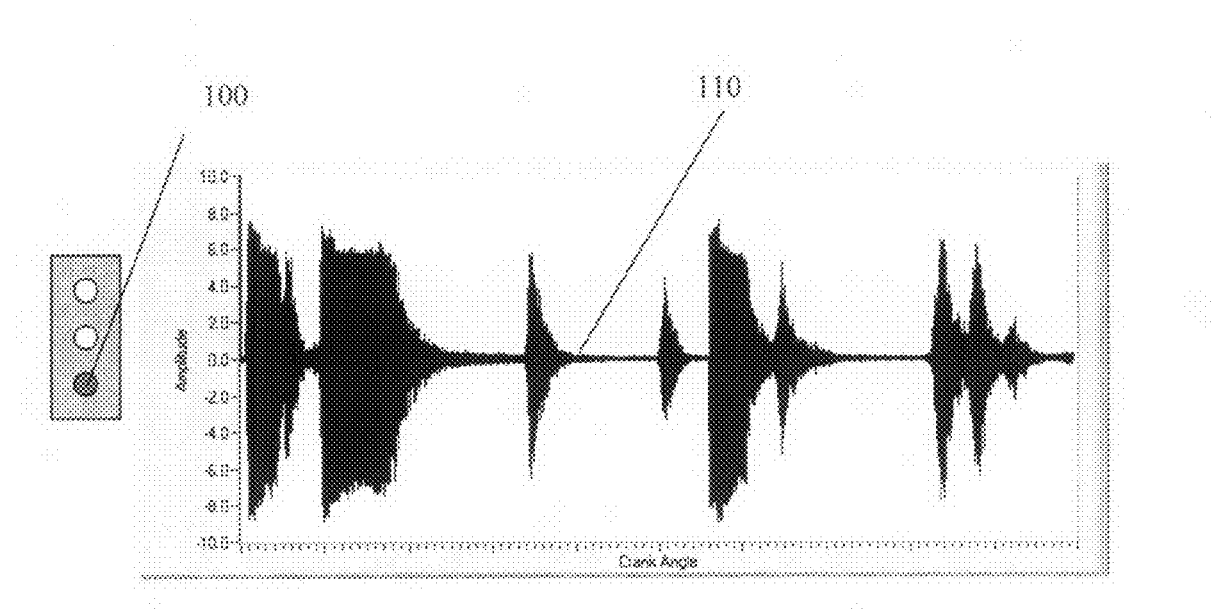
FIGS. 10 to 13 are screenshots of an alternate user interface of the alert generation system according to another embodiment of the present invention.

FIG. 10 shows a normal valve fingerprint 110 and no associated alert from the traffic lights (green light 100).

Figure 11:
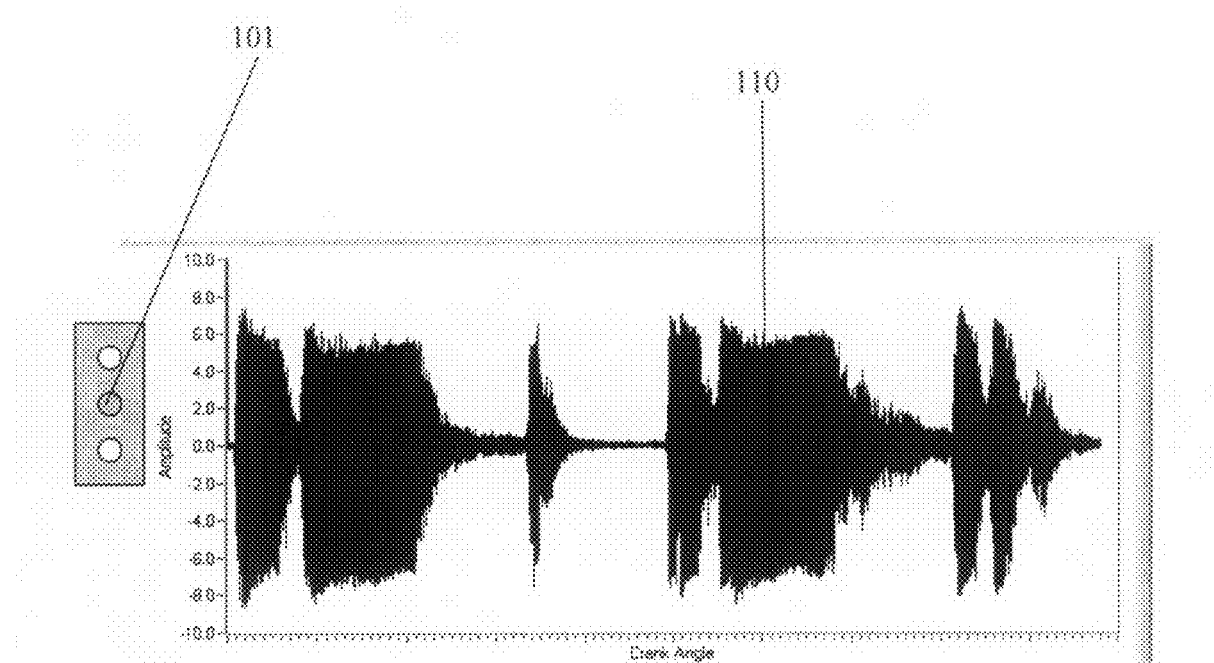

FIG. 11 shows a fingerprint 110 resulting from a slight cut in suction spring/ring (gas leakage) and an associated alert (amber traffic light 101 displayed).

Figure 12:
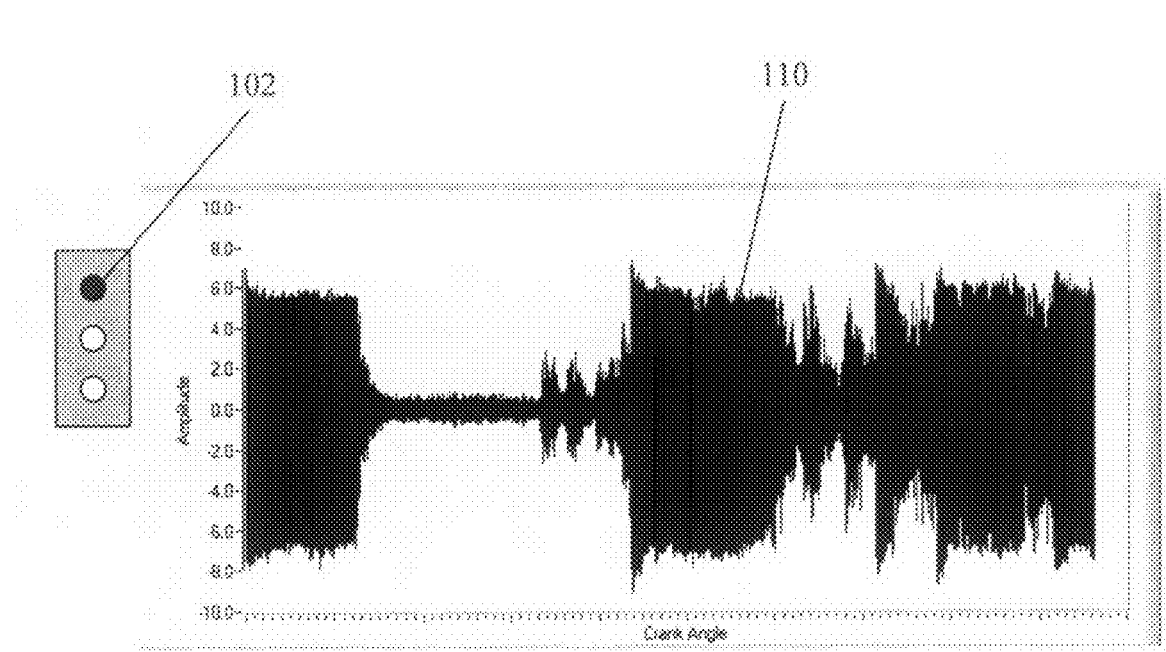

FIG. 12 shows a fingerprint 110 resulting from a centre cut in suction valve spring (excessive leakage/energy throughout the cycle) and an associated alert (red traffic light 102 displayed).

Figure 13:
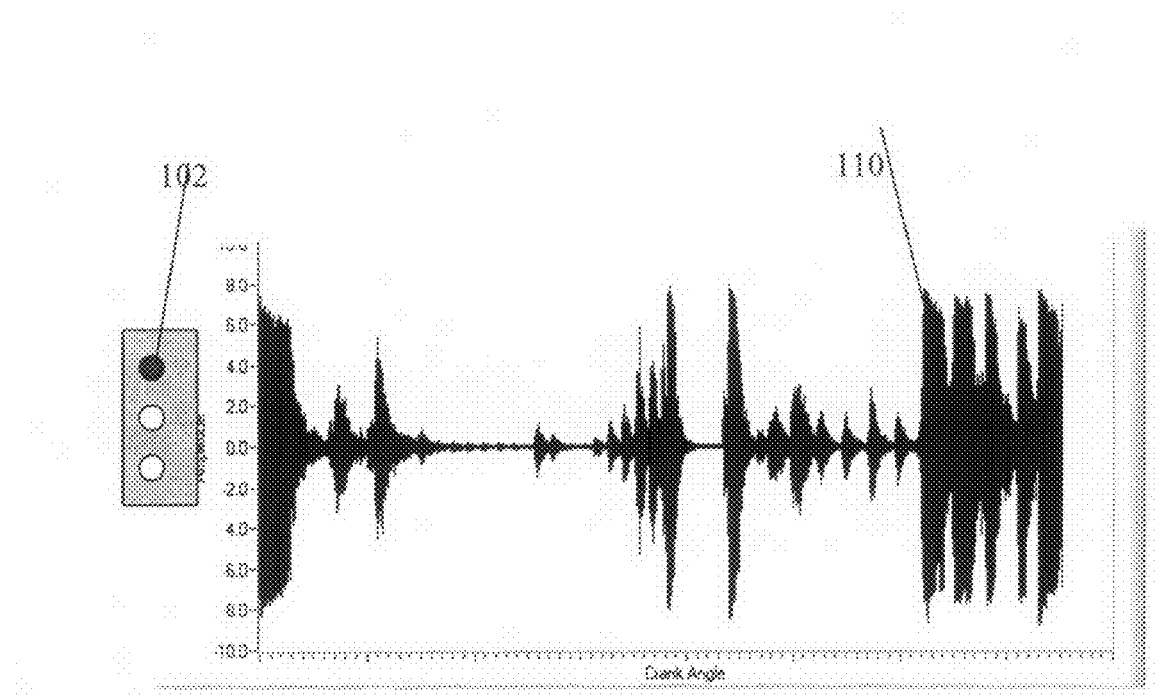

FIG. 13 shows a fingerprint 110 resulting from speed and pressure fluctuations (excessive valve flutter/pulsation) and an associated alert (red traffic light 102 displayed.

The importance of the alert is categorised by the colour of the traffic light 1(red being more important than amber, green being no alert). It may be that an overall machine or system has an associated traffic light that a user can drill down upon to determine the source of an alert.

Figure 14:
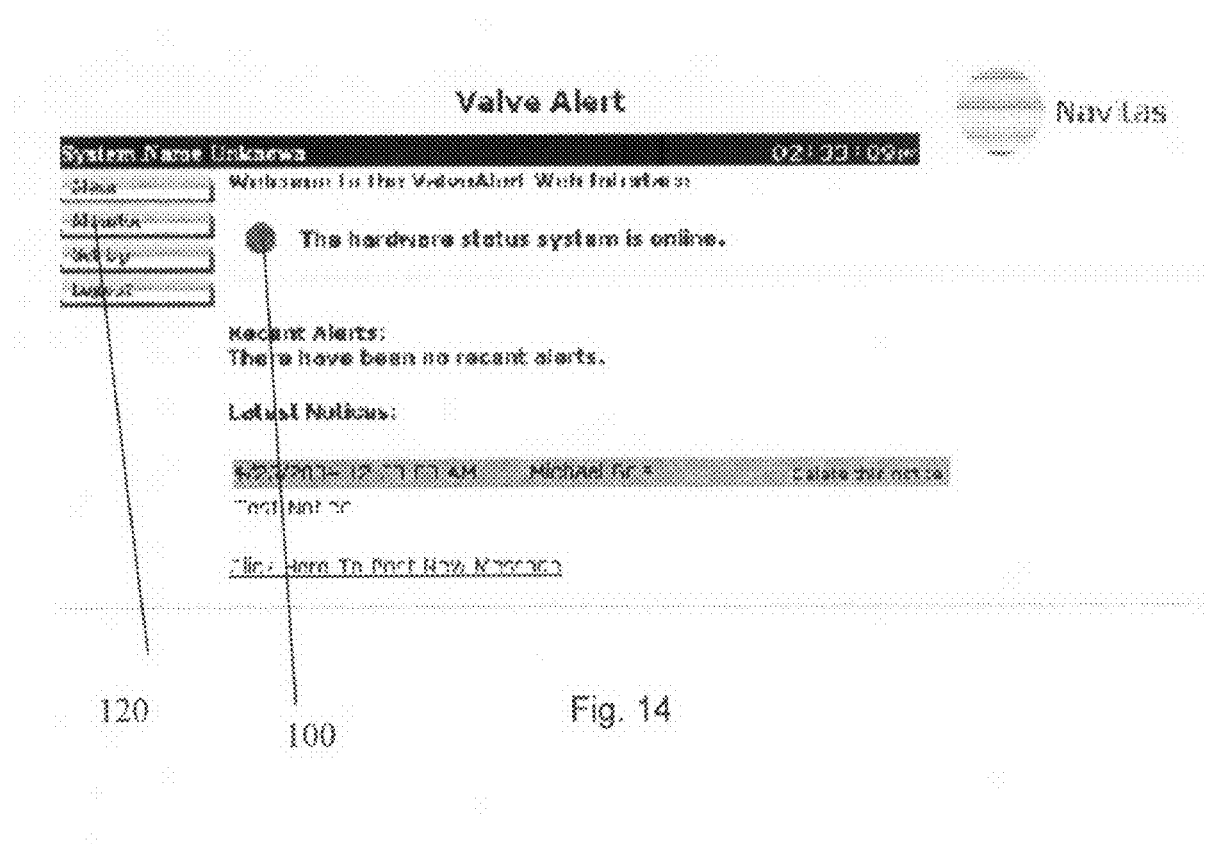

FIGS. 14 to 25 are screen shots from an alternative online user interface provided by the alert generation system. The user interface is generated by a web server and can be accessed over an intranet or the internet via any web browser. Upon logging in to the system, the user is presented with an overall system status as is shown in FIG. 14. Next to the status (in this case "the hardware status system is online") an alert indicator 100 is shown—in this case it is green indicating that the system is ok.

Figure 15:
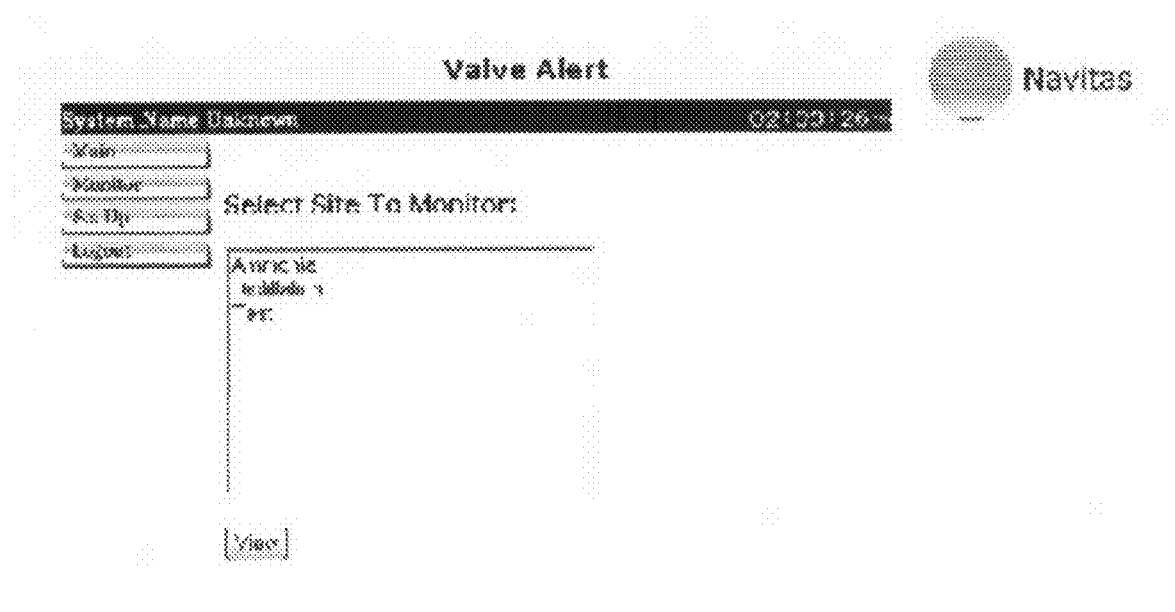

When the user clicks the "monitor" button 120, if more than one site can be monitored then the user is prompted to pick a site, as is shown in FIG. 15.

Figure 16:
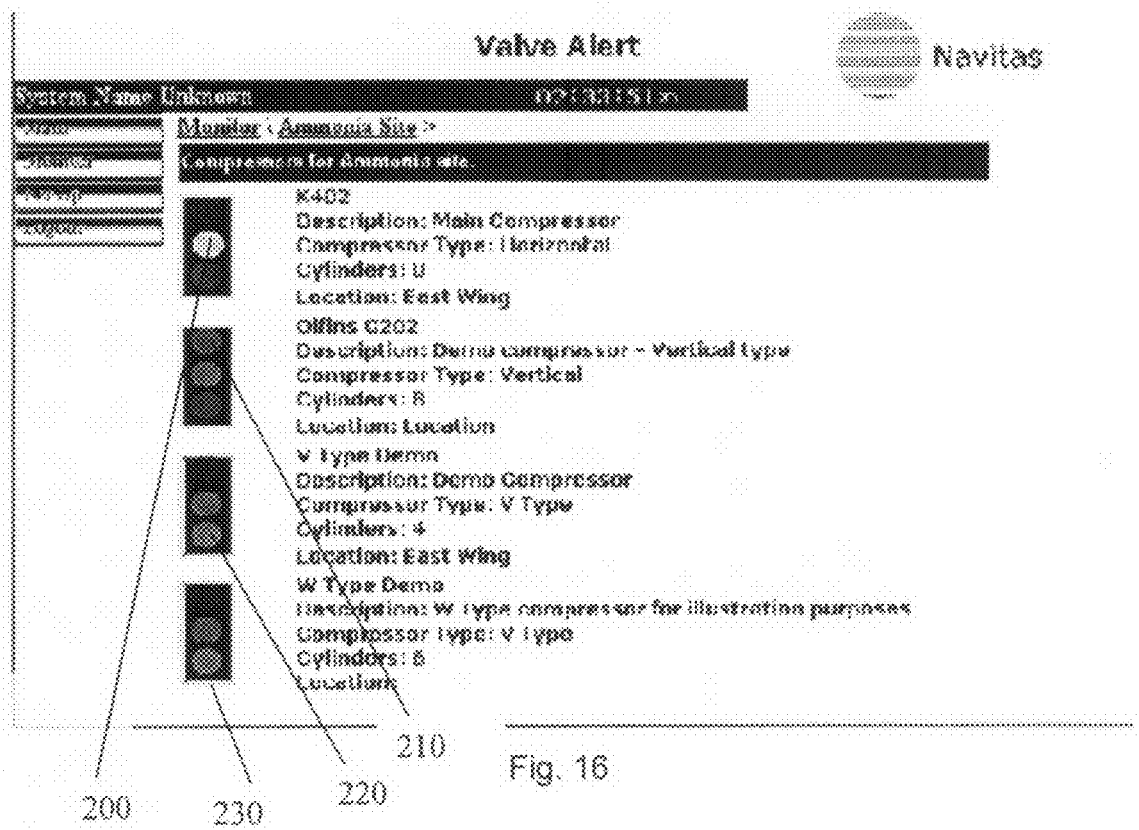

Upon picking the Ammonia site, the user is presented with a status of compressors for the site, as is shown in FIG. 16. The status shows an alert indicator (the traffic lights on the left hand side) along with a description of each compressor opposite the alert indicator. The first alert indicator 200 for the K402 compressor is displaying amber (moderate alert), the second 210 for the Olefins C202 is displaying red (serious alert) whilst the other two indicators 220, 230 are green.

Figure 17:
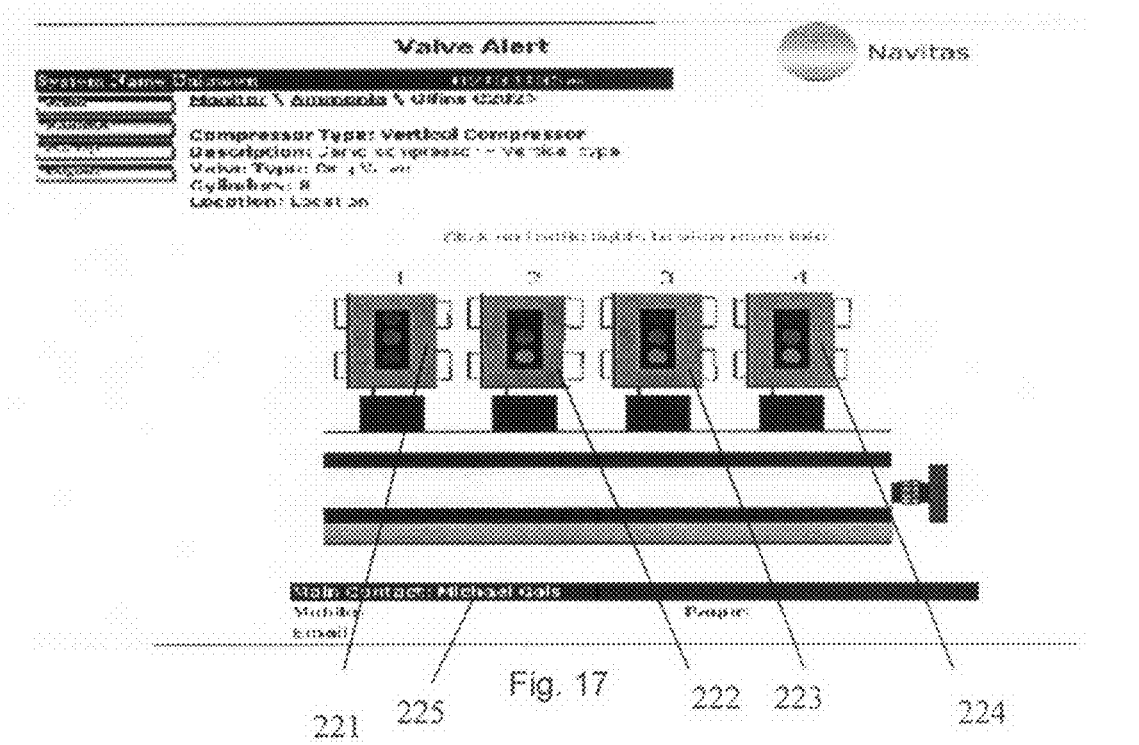

Upon clicking on the second alert indicator 210, a graphical representation of the compressor and valve status is displayed, as is shown in FIG. 17. Valves 222-224 are green (ok) but valve 221 is showing a red alert light. Immediately below the representation is a space 225 for contact information for a user to contact for technical support regarding the valve (for example, contact information for a supervisor or valve technician responsible).

Figure 18:
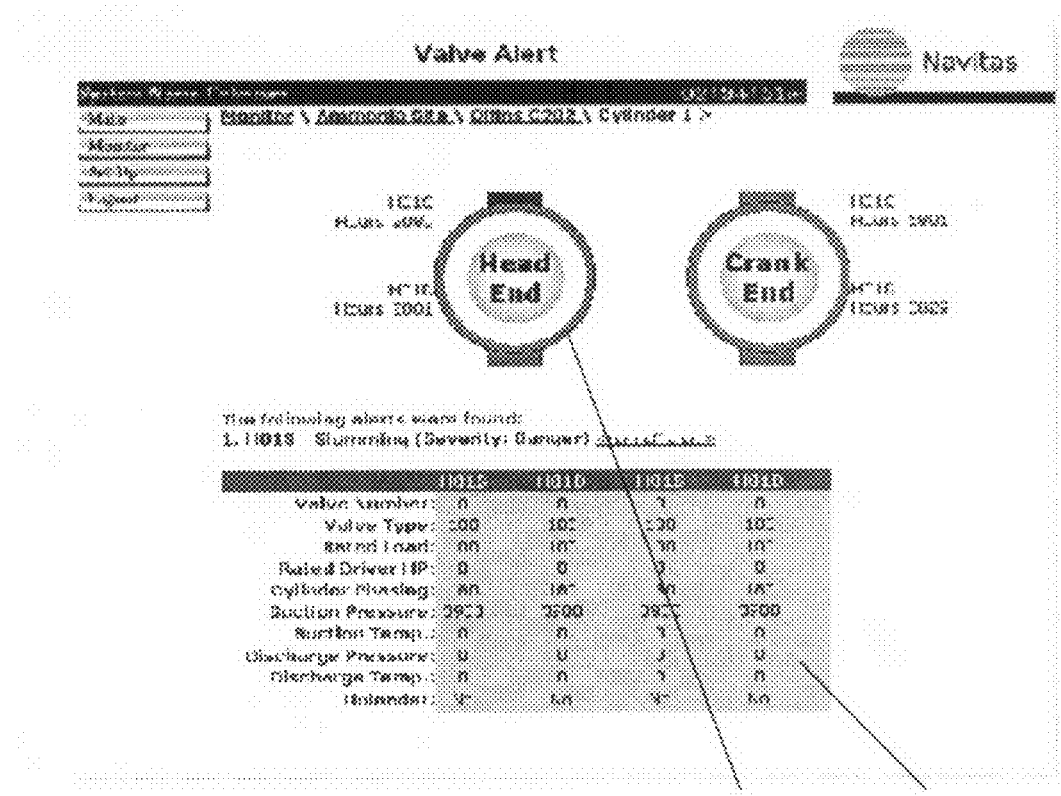

Upon clicking on the first valve indicator, detailed information on the valve is displayed, as is shown in FIG. 18. This information shows that element H01S is slamming and the relevant area 250 of the graphical representation is highlighted red to show the severity of the problem. Measurement data 260 is also displayed.

Figure 19:
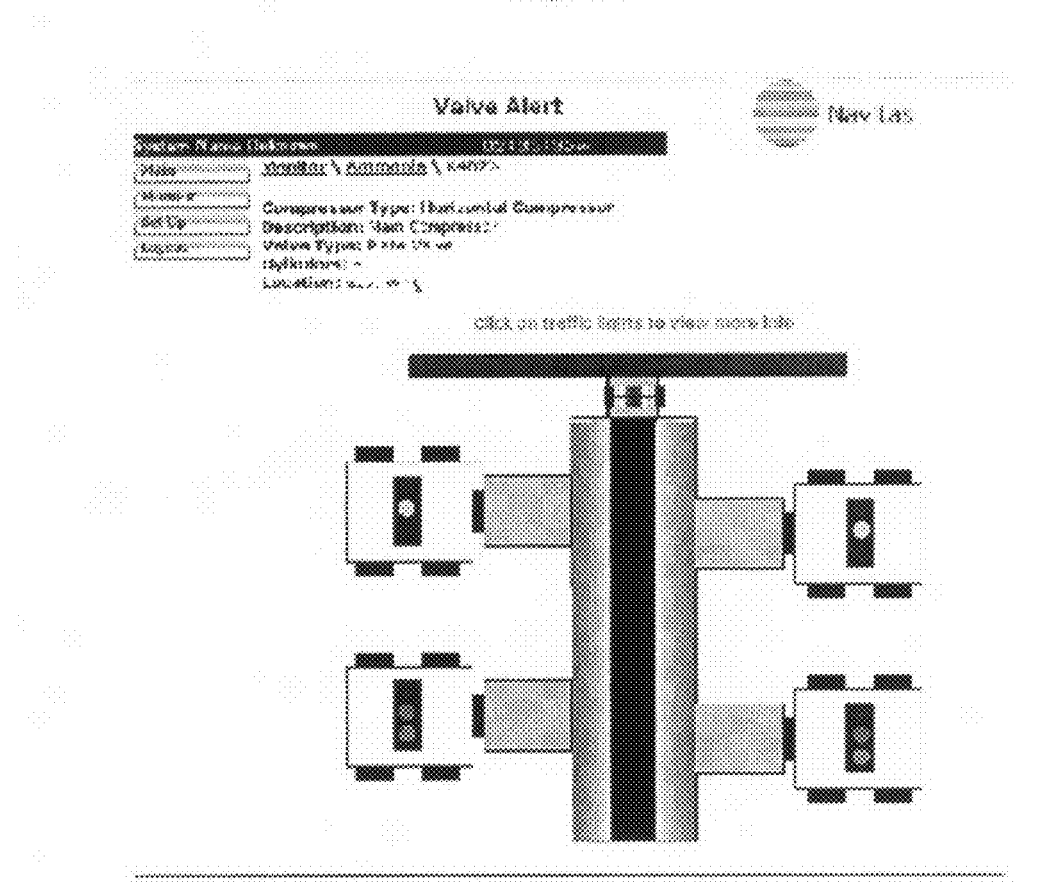
Figure 20:
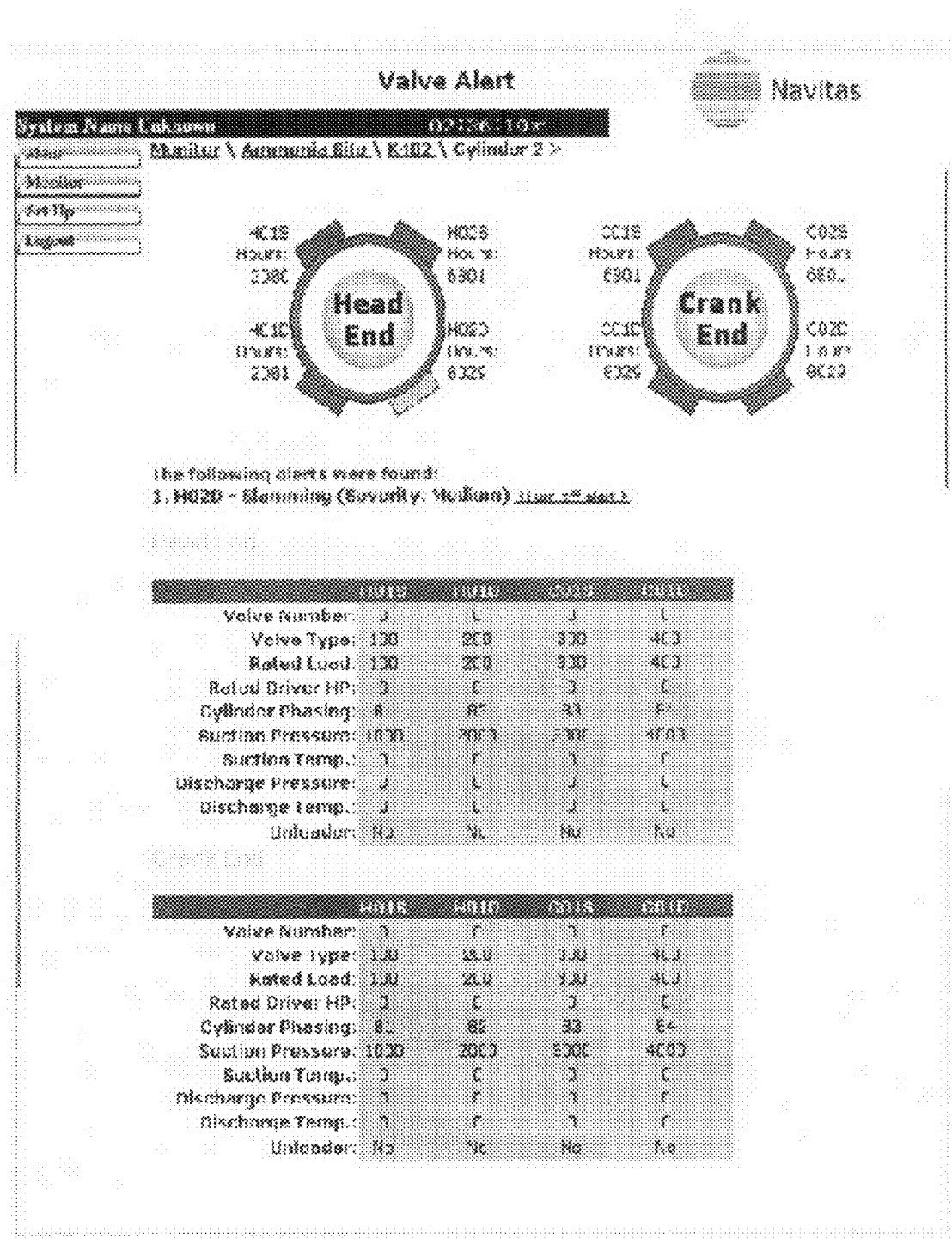

Drilling down into the K402 compressor shows a different representation corresponding to the compressor type, as is shown in FIG. 19. In this case, cylinders 1 and 2 are highlighted amber. Drilling down into cylinder 2, element H02D is shown to be slamming with a medium severity, as can be seen from FIG. 20.

Figure 21:
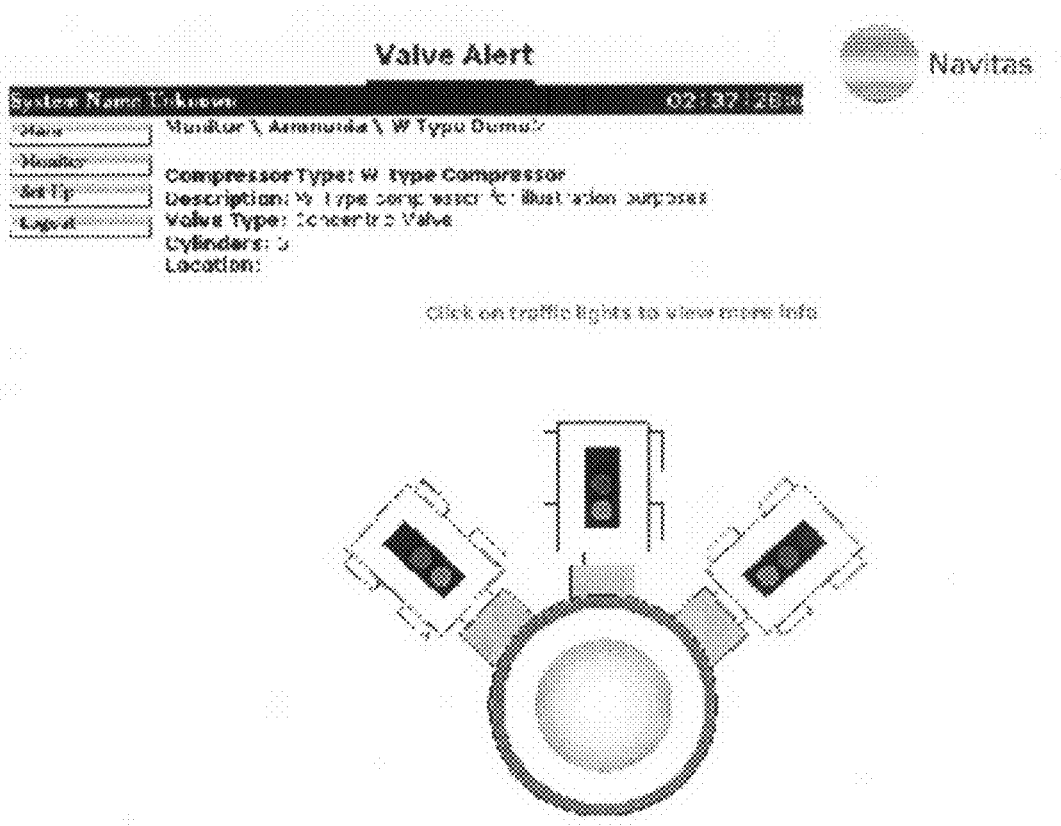
Figure 22:
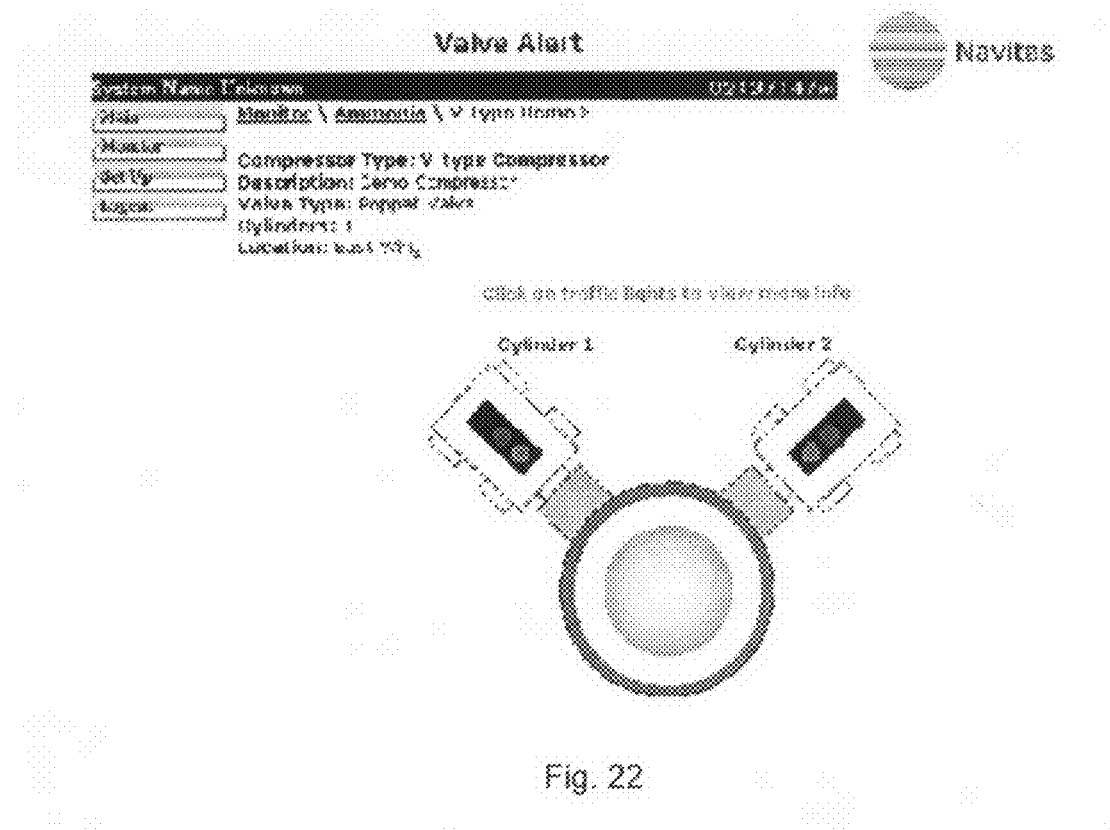

FIGS. 21 and 22 show the other 2 compressors of the Ammonia site—each having a different configuration and therefore a different graphical representation. The cylinders and valves could be drilled down in a similar manner to those discussed above.

Figure 23:
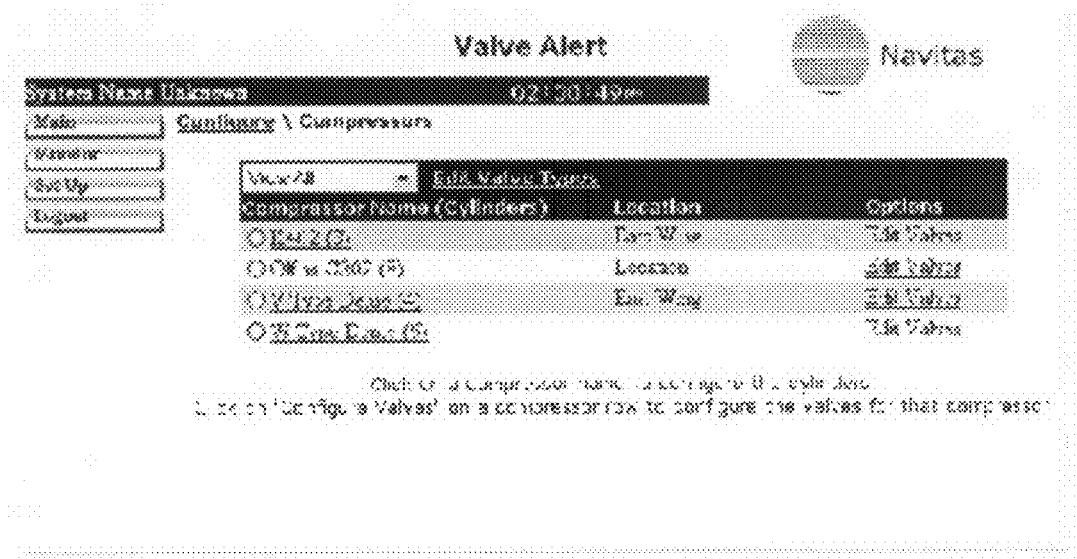
Figure 24:
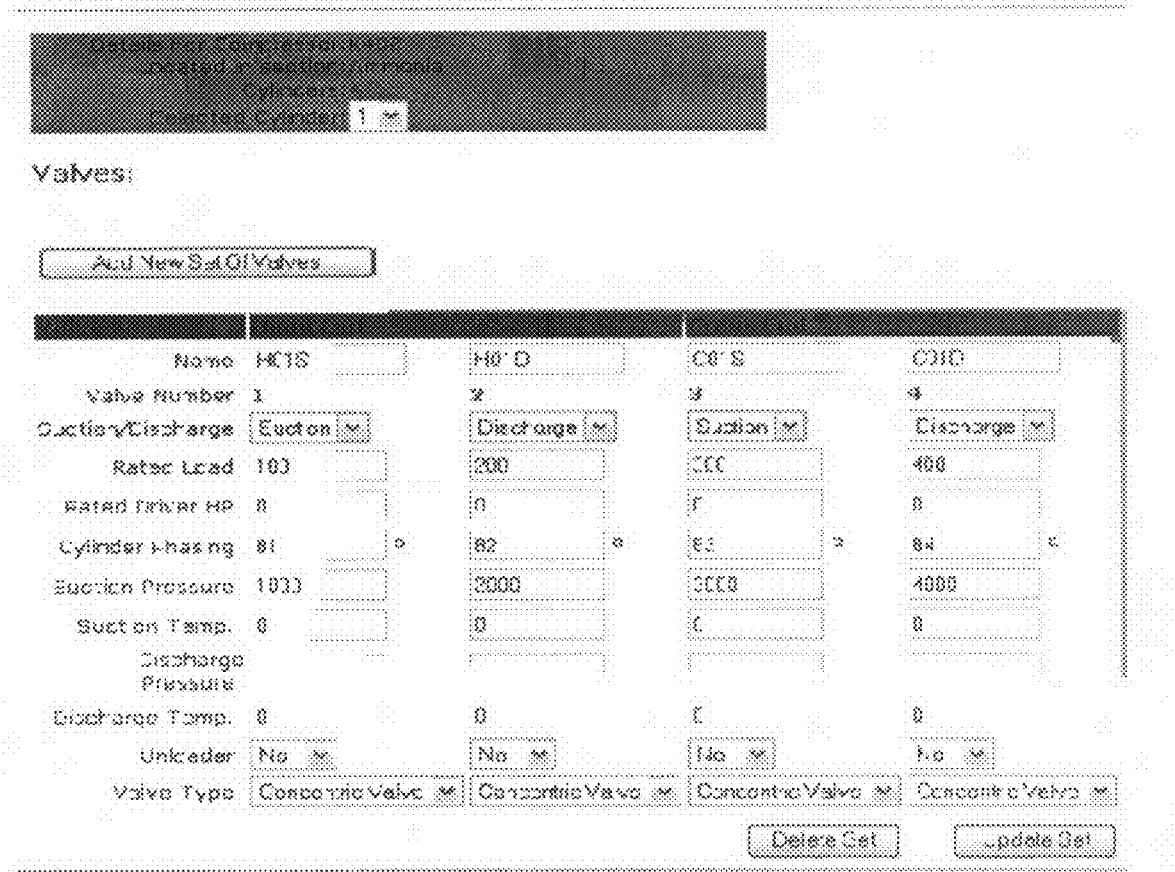

Upon clicking setup, an authorised user is offered various system components that can be set up. FIGS. 23 and 24 show screens in which compressors can be defined and set up whilst FIG. 25 shows a screen in which various alerts can be defined and notifications associated with the alerts so warning emails/text messages can be sent to those responsible if an amber/red alert status is detected.

Figure 27:
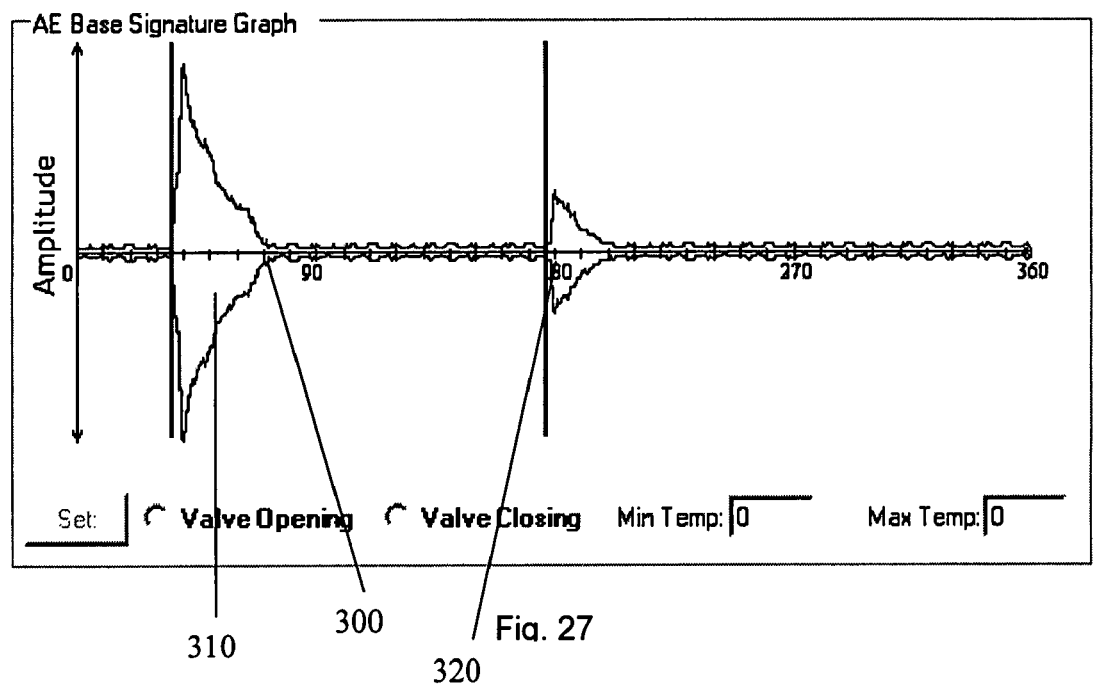
Figure 28:
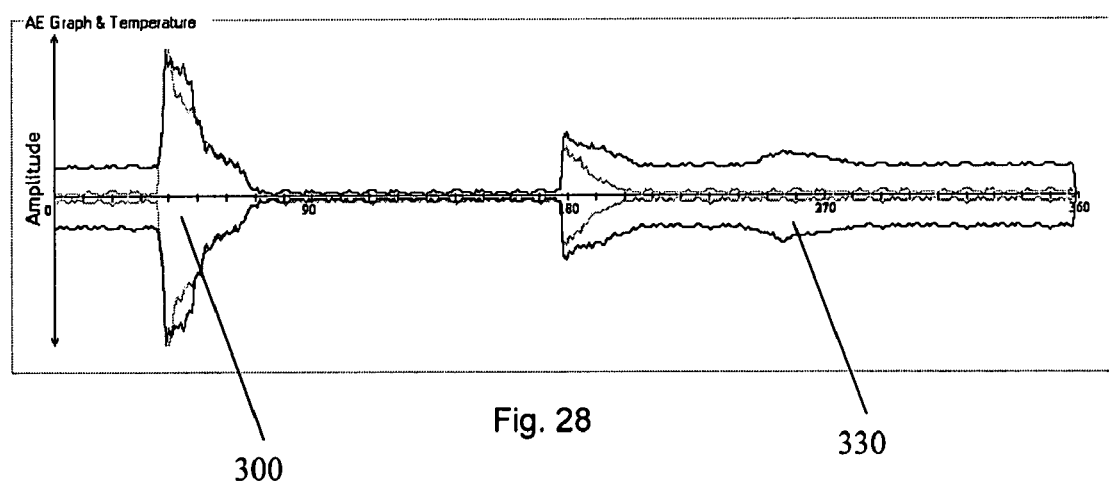
Figure 29:
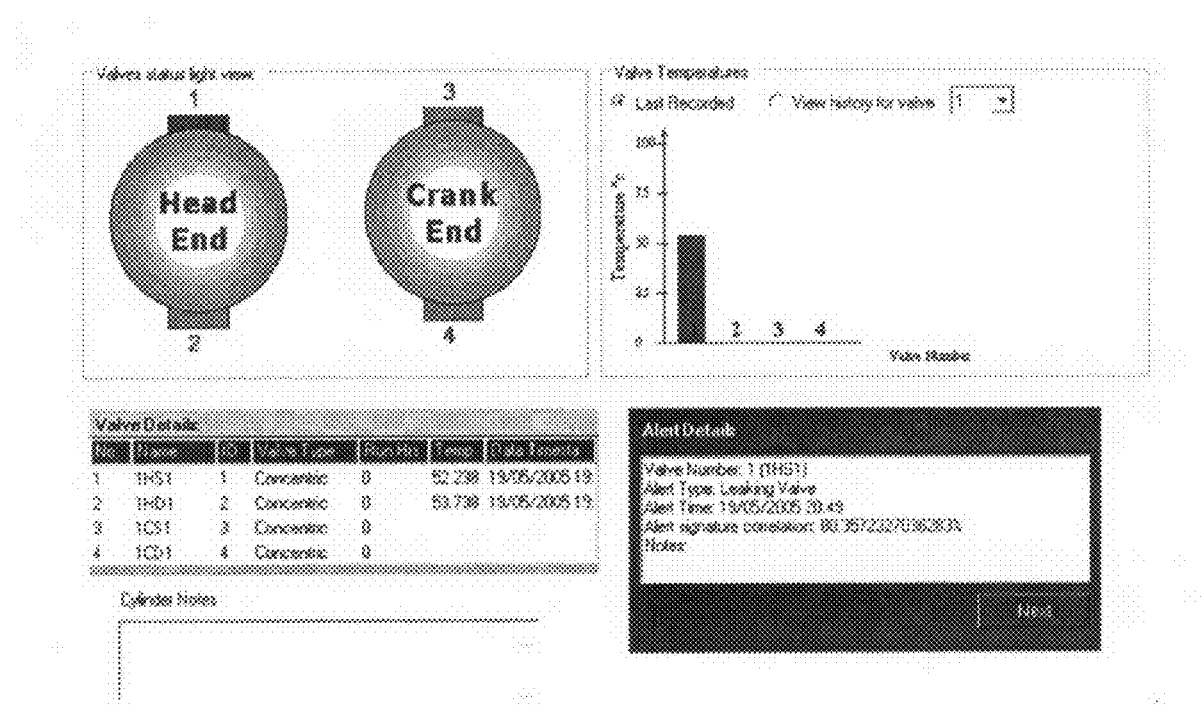

FIGS. 26 to 29 show an alternate layout of a user interface provided by the alert generation system. In FIG. 26, the baseline fingerprint 300 for a valve is shown. In FIG. 27, valve opening and closing positions are indicated by lines 310 and 320. In FIG. 28, a further acoustic signal 330 is overlaid over the baseline fingerprint 300 to show changes to the user. In FIG. 29, detailed analysis on the further acoustic signal 330 and valve status is provided.

A number of steps are taken to install a system according to an embodiment of the present invention at a site including:

1. Initial Set-Up

A once-per-turn marker is installed on the compressor flywheel to allow a user of a portable data collector to know when a complete cycle has been made, thus indicating that sufficient data has been captured for analysis. In addition, sensors are fixed onto the compressor valve caps.

2. Define/Set-Up Software

The compressor cylinder and valve assemblies are identified and analysed in order to properly assess wave propagation and sensor placement issues. This includes definition of the range of field measurements to be made at
   Initial field evaluation
   Subsequent "routine" tests.

One sensor per valve was fitted to the 1st stage suction and discharge valve caps only and all cables then connected to the system instrumentation.

3. Initial Tests/Evaluation:

A normal valve fingerprint is captured for the stationary compressor. Assuming this is satisfactory, this is used as the baseline for subsequent analysis.

During operation, a number of valve anomalies could be encountered including:
   1. Valve with stiff springs
   2. Valve with weak springs
   3. Valve with slight cut in plate
   4. Valve with small section cut on the outside spring 5. Valve with centre section broken (typical failure on Mehrer valve)

Valve with Stiff Springs: (Suction Valve)
Valve demonstrated slight change in the energy compared to normal valve dynamics, energy fingerprint detected was sufficient tot trigger an alarm.

Valve with Weak Spring: (Discharge Valve)
Valve demonstrated slight change in the energy compared to normal valve dynamics, energy fingerprint differences were sufficient to trigger an alarm.

Valve with Slight Cut in Plate: (Suction Valve Modified)
Valve demonstrated slight change in the energy to normal valve dynamics. Energy fingerprint differences due to the crack propagation were sufficient to trigger an alarm.

Valve with Outer Section Cut (Suction Valve Modified)
Valve demonstrated slight change in the energy to normal valve dynamics. Energy fingerprint differences were sufficient to trigger an alarm.

Valve with Centre Section Broken (Suction Valve Modified)
Valve demonstrated slight change in the energy to normal valve dynamics. Energy fingerprint differences were sufficient to trigger an alarm Speed and Pressure Changes (Good Valves Suction and Discharge)
The valve(s) demonstrated significant valve flutter/pulsations. Energy fingerprint differences were sufficient to trigger an alarm.

Speed and Pressure Changes (Good Valves Suction and Discharge)
The valve(s) demonstrated slight valve flutter/pulsations. Energy fingerprint differences were sufficient to trigger an alarm.

Speed and Pressure Changes (Good Valves Suction and Discharge)
Valve(s) demonstrated significant valve flutter/pulsations. Energy fingerprint differences were sufficient to trigger an alarm.

Valve with Slight Cut in Plate: (Discharge Valve Modified)
Valve demonstrated slight change in the energy to normal valve dynamics. Energy fingerprint differences were sufficient to trigger an alarm.

Valve with Outer Section Cut (Discharge Valve Modified)
Valve demonstrated slight change in the energy to normal valve dynamics. Energy fingerprint differences were sufficient to trigger an alarm.

Valve with Centre Section Broken (Discharge Valve Modified)
Valve demonstrated significant change in the energy to normal valve dynamics. Energy fingerprint differences were sufficient to trigger an alarm.

It would be preferred if sensors capable of filtering out cross talk from the valves were used as the close proximity of the valves can create inherent noise and cross talk.

In addition valve anomalies could be detected using only 2 sensors for 4 valves on certain compressors.

Subtle cracks that appear in the valves at an early stage produce sufficient energy to enable the system's algorithms to apply the appropriate alarm in advance of any failure. Without any means of analysis these types of anomalies would not be detected until it was to late.

In most cases the system can identify piston ring leakage in addition to the valve anomalies.

Whilst various sensor arrangements are possible, a preferred arranged ement is discussed below:

A sensor is preferably a small device with a microcontroller, a radio frequency transceiver and 2 sensing systems. The first of the sensing systems is an acoustical emission (AE) sensor for monitoring the valve vibrations, and the second is a temperature sensing system for monitoring the external valve surface temperature. Since the range of vibrations from the valves can vary from one valve/compressor to another, an amplifier with gain control is used to regulate the voltages from the AE sensor to the ADC. The ADC converts these voltages into digital values, which are stored into temporary memory registers in the microcontroller. The microcontroller is responsible for obtaining this data and ensuring that it is relayed to the central monitoring station for analysis. In the event that it cannot send the data, the data is stored in an internal buffer until data transfer is possible, or until the next set of measurements are taken, whichever occurs first. The microcontroller is responsible for implementing the wireless communication protocol in order to communicate with the central monitoring station. The microcontroller must consume very little power since the sensor nodes will be running on batteries.

Acoustic Emission (AE) Measurements:
Data Measured: The vibrations of the external valve surface must be monitored for a minimum of one entire rotation of the compressor flywheel.
Frequency of measurements: At least one sample of data each minute, every minute.
Limitations: AE sensor measurements maximum bandwidth: 150 kHz
Maximum flywheel RPM: 1500
Data Processing: AE measurements must be envelope detected and 450 samples taken of one complete flywheel rotation.
Minimum ADC sampling resolution: 10 bits
Minimum ADC sampling rate (Nyquist): 22.5 kHz
Temperature Measurements:
Data Measured: The external valve surface temperature.
Frequency of measurements: At least once per minute
Limitations: Range of temperatures to monitor: 20° C. to 60° C.

Although the embodiments of the present invention above have been described with reference to hardware and software, it will be apparent that other implementations of the present invention are possible and fall within the scope of the appended claims. For example, software could be substituted for hardware, firmware or a mixture of such components.

The invention claimed is:

1. A valve monitoring system including an alert generation system, a user interface, and a memory, wherein:
   a. the memory encodes baseline acoustic emission data on the valve for a predetermined period of operation,
   b. the alert generation system is arranged to receive acoustic emission data for the valve, compare the received acoustic emission data for the valve with the baseline acoustic emission data encoded in the memory and identify valve anomalies in dependence on differences in the received acoustic emission data and the baseline acoustic emission data,
   c. the user interface is arranged to visually display an indication of the anomalies identified for the valve, wherein the indication comprises a hierarchy of warning lights, the warning light illuminated being dependent on the severity of the anomaly identified.

2. A valve monitoring system according to claim 1, wherein the valve is mounted in a reciprocating compressor, the predetermined period of operation comprising a 360° rotation of the crank of the reciprocating compressor.

3. A valve monitoring system according to claim 1, further comprising a sensor mounted to obtain acoustic emission data on the valve and a data collector arranged to communicate with the sensor to obtain said acoustic emission data.

4. A valve monitoring system according to claim 3, wherein the data collector comprises a portable device and includes an input device for receiving an identifier for the valve to which a sensor is mounted, a memory for storing said identifier and said acoustic emission data and at least one communication system for communicating with the sensor and the alert generation system.

5. A valve monitoring system according to claim 4, wherein the identifier includes a barcode displayed in a location near to the valve, the data collector including a barcode reader.

6. A valve monitoring system according to claim 4, wherein the identifier includes an RFID tag integrated into said sensor, the data collector including an RFID tag reader.

7. A valve monitoring system according to claim 4, wherein the portable device includes a processor arranged to remove negative waveform components and high frequency carrier components of the acoustic emission data prior to storage in the memory.

8. A valve monitoring system according to claim 3, wherein the alert generation system and memory are remote from the sensor and data collector is integrated with the sensor, the data collector including a communications system to communicate said acoustic emission data to the alert generation system.

9. A valve monitoring system according to claim 6, further comprising a plurality of data collectors and a plurality of intermediate nodes, each of said plurality of data collectors being arranged to communicate its acoustic emission data to a predetermined one of said plurality of intermediate nodes, each intermediate node being arranged to communicate received acoustic emission data to said alert generation system.

10. A valve monitoring system according to claim 8, wherein the data collector includes a processor arranged to remove negative waveform components and high frequency carrier components of the acoustic emission data prior to communication of the acoustic emission data.

11. A valve monitoring system according to claim 1, further comprising an alert notification system arranged to provide notification to a contact associated with said valve in response to identification of a valve anomaly, notification comprising at least one of:
an email message, an instant message, an SMS message or a pre-recorded telephone message.

12. A valve monitoring system according to claim 1, wherein the user interface includes a schematic representation of monitored valves, the schematic representation being visually associated with the indication for the respective valve.

13. In a valve monitoring system, a method for monitoring valves comprises:
obtaining a baseline acoustic emission signal for a valve for a predetermined period of operation;
obtaining a further acoustic emission signal for the valve for the predetermined period of operation;
comparing the baseline acoustic emission signal with the further acoustic emission signal;
identifying valve anomalies in dependence on differences between the baseline acoustic emission signal and the further acoustic emission signals;
visually displaying, on a user interface, an indication of the identified valve anomalies, wherein the indication comprises a hierarchy of warning lights, the warning light illuminated being dependent on the severity of the anomaly identified.

14. In a valve monitoring system, the method for monitoring valves of claim 13 further comprises:
mounting an acoustic emission sensor on a valve of a reciprocating compressor, wherein the predetermined period of operation comprises a 360° rotation of the crank of the reciprocating compressor.

15. In a valve monitoring system, the method for monitoring valves of claim 14 further comprises:
collecting the further acoustic emission signal from the sensor using a portable data collector arranged to communicate with the sensor; and,
downloading the acoustic emission signal from the portable data collector to a system remote to the sensor for said comparison and identification steps.

16. In a valve monitoring system, the method for monitoring valves of claim 15 further comprises:
removing negative waveform components and high frequency carrier components of the further acoustic emission signal prior to downloading.

17. In a valve monitoring system, the method for monitoring valves of claim 14 further comprises:
collecting the further acoustic emission signal from the sensor at a data collector integrated with the sensor and mounted on the valve; and,
transmitting the acoustic emission signal to a system remote to the sensor for said comparison and identification steps.

18. In a valve monitoring system, the method for monitoring valves of claim 17 further comprises:
removing negative waveform components and high frequency carrier components of the further acoustic emission signal prior to transmitting.

19. In a valve monitoring system, the method for monitoring valves of claim 13 further comprises:
visually displaying, on the user interface, a schematic representation of monitored valves, the schematic representation being visually associated with the indication for the respective valve.

20. A valve monitoring system including an alert generation system, a user interface, and a memory, wherein:
a. the memory encodes baseline acoustic emission data on the valve for a predetermined period of operation,
b. the alert generation system is arranged to receive acoustic emission data for the valve, compare the received acoustic emission data for the valve with the baseline acoustic emission data encoded in the memory and identify valve anomalies in dependence on differences in the received acoustic emission data and the baseline acoustic emission data,
c. the user interface includes a schematic representation of monitored valves, the schematic representation being visually associated with the indication for the respective valve.

* * * * *